(12) United States Patent
Mizuki et al.

(10) Patent No.: US 10,964,891 B2
(45) Date of Patent: Mar. 30, 2021

(54) PYRENE DERIVATIVE, ORGANIC LIGHT-EMITTING MEDIUM, AND ORGANIC ELECTROLUMINESCENT ELEMENT CONTAINING PYRENE DERIVATIVE OR ORGANIC LIGHT- EMITTING MEDIUM

(71) Applicant: Idemitsu Kosan Co., Ltd., Tokyo (JP)

(72) Inventors: Yumiko Mizuki, Sodegaura (JP); Hirokatsu Ito, Sodegaura (JP); Takeshi Ikeda, Sodegaura (JP); Hiroyuki Saito, Sodegaura (JP); Masahiro Kawamura, Sodegaura (JP); Yuichiro Kawamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 16/020,746

(22) Filed: Jun. 27, 2018

(65) Prior Publication Data
US 2018/0309058 A1   Oct. 25, 2018

Related U.S. Application Data

(63) Continuation of application No. 14/112,497, filed as application No. PCT/JP2012/002578 on Apr. 13, 2012, now Pat. No. 10,014,476.

(30) Foreign Application Priority Data

Apr. 18, 2011   (JP) ................................ 2011-092380

(51) Int. Cl.
| | | |
|---|---|---|
| *H01L 51/00* | (2006.01) | |
| *C07F 7/08* | (2006.01) | |
| *C09K 11/06* | (2006.01) | |
| *C07C 13/567* | (2006.01) | |
| *C07C 13/66* | (2006.01) | |

(Continued)

(52) U.S. Cl.
CPC .......... *H01L 51/006* (2013.01); *C07C 13/567* (2013.01); *C07C 13/66* (2013.01); *C07C 15/20* (2013.01); *C07C 15/24* (2013.01); *C07C 15/30* (2013.01); *C07C 15/38* (2013.01); *C07C 211/61* (2013.01); *C07C 217/92* (2013.01); *C07C 255/58* (2013.01); *C07D 209/88* (2013.01); *C07D 213/38* (2013.01); *C07D 215/38* (2013.01); *C07D 235/18* (2013.01); *C07D 307/91* (2013.01); *C07F 7/081* (2013.01); *C09K 11/06* (2013.01); *C07C 2601/14* (2017.05); *C07C 2603/18* (2017.05); *C07C 2603/24* (2017.05); *C07C 2603/26* (2017.05); *C07C 2603/40* (2017.05); *C07C 2603/42* (2017.05); *C07C 2603/50* (2017.05); *C07C 2603/52* (2017.05); *C07C 2603/86* (2017.05); *C09K 2211/1007* (2013.01); *C09K 2211/1011* (2013.01); *C09K 2211/1022* (2013.01);

(Continued)

(58) Field of Classification Search
CPC ........................... H01L 51/0065; C07C 13/567
See application file for complete search history.

(56) References Cited

U.S. PATENT DOCUMENTS

| | | | |
|---|---|---|---|
| 7,700,201 B2 | 4/2010 | Seo et al. | |
| 7,839,074 B2 | 11/2010 | Ikeda et al. | |

(Continued)

FOREIGN PATENT DOCUMENTS

| | | |
|---|---|---|
| JP | 2004-204238 A | 7/2004 |
| JP | 2004-224723 A | 8/2004 |

(Continued)

OTHER PUBLICATIONS

MT of WO2009069537, no date.*

(Continued)

*Primary Examiner* — Alex A Rolland
(74) *Attorney, Agent, or Firm* — Foley & Lardner LLP

(57) ABSTRACT

An organic light-emitting medium including a pyrene derivative represented by the following formula (1) and a phenyl-substituted anthracene derivative represented by the following formula (2):

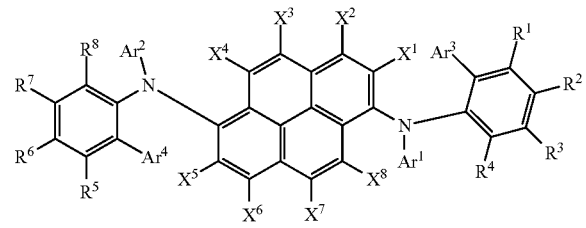

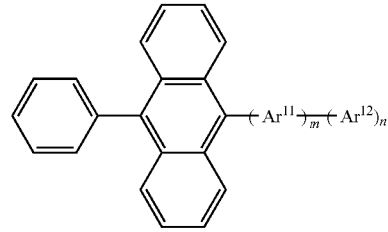

wherein $Ar^1$ to $Ar^4$ are independently a substituted or unsubstituted aryl group having 6 to 30 ring carbon atoms or a substituted or unsubstituted heteroaryl group having 5 to 20 ring atoms.

8 Claims, No Drawings

(51) Int. Cl.
- *C07C 15/20* (2006.01)
- *C07C 15/24* (2006.01)
- *C07C 15/30* (2006.01)
- *C07C 15/38* (2006.01)
- *C07C 255/58* (2006.01)
- *C07C 211/61* (2006.01)
- *C07C 217/92* (2006.01)
- *C07D 215/38* (2006.01)
- *C07D 235/18* (2006.01)
- *C07D 209/88* (2006.01)
- *C07D 213/38* (2006.01)
- *C07D 307/91* (2006.01)
- *H01L 51/50* (2006.01)

(52) U.S. Cl.
CPC ............... *C09K 2211/1029* (2013.01); *C09K 2211/1088* (2013.01); *H01L 51/5012* (2013.01)

(56) References Cited

U.S. PATENT DOCUMENTS

| | | |
|---|---|---|
| 8,318,324 B2 | 11/2012 | Ikeda et al. |
| 8,431,250 B2 | 4/2013 | Mizuki et al. |
| 8,436,344 B2 | 5/2013 | Seo et al. |
| 2006/0043858 A1 | 3/2006 | Ikeda et al. |
| 2007/0252511 A1 | 11/2007 | Funahashi |
| 2011/0042660 A1* | 2/2011 | Kawamura ............ C09K 11/06 257/40 |
| 2012/0001161 A1 | 1/2012 | Nakano et al. |
| 2012/0235561 A1 | 9/2012 | Ikeda et al. |
| 2013/0153878 A1 | 6/2013 | Mizuki et al. |

FOREIGN PATENT DOCUMENTS

| | | | |
|---|---|---|---|
| JP | 2004224723 A * | 8/2004 | |
| JP | 2010-053131 A | 3/2010 | |
| JP | 2011-153201 A | 8/2011 | |
| WO | WO-2004/018587 A1 | 3/2004 | |
| WO | WO-2005/108348 A1 | 11/2005 | |
| WO | WO-2009/069537 A1 | 6/2009 | |
| WO | WO-2009069537 A1 * | 6/2009 | ........... C07D 307/91 |
| WO | WO-2009/102054 A1 | 8/2009 | |
| WO | WO-2009102054 A1 * | 8/2009 | ............. C09K 11/06 |
| WO | WO-2010/113743 A1 | 10/2010 | |
| WO | WO-2010/122810 A1 | 10/2010 | |

OTHER PUBLICATIONS

International Preliminary Report on Patentability in PCT/JP2012/002578 dated Oct. 31, 2013.
International Search Report received in PCT/JP2012/002578 dated Jun. 5, 2012.
U.S. Office Action on U.S. Appl. No. 14/112,497 dated Jun. 22, 2016.
U.S. Office Action on U.S. Appl. No. 14/112,497 dated Aug. 18, 2017.

* cited by examiner

PYRENE DERIVATIVE, ORGANIC LIGHT-EMITTING MEDIUM, AND ORGANIC ELECTROLUMINESCENT ELEMENT CONTAINING PYRENE DERIVATIVE OR ORGANIC LIGHT- EMITTING MEDIUM

TECHNICAL FIELD

The invention relates to a pyrene derivative, an organic light-emitting medium and an organic electroluminescence medium containing them.

BACKGROUND ART

An organic electroluminescence (EL) device using an organic substance is a promising solid-state emitting type inexpensive and large full-color display device, and has been extensively developed. In general, an organic EL device includes an emitting layer and a pair of opposing electrodes holding the emitting layer therebetween. When an electric field is applied between the electrodes, electrons are injected from the cathode and holes are injected from the anode. The electrons recombine with the holes in the emitting layer to produce an excited state, and energy is emitted as light when the excited state returns to the ground state.

With an improvement in technology of prolonging the lifetime, an organic EL device of recent years are being applied to a full-color display such as a mobile phone or a TV, and the performance of an organic EL device has been gradually improved with improvements in emitting materials for an organic EL device.

For example, in Patent Documents 1 to 3, a combination of an anthracene host with a specific structure and a diaminopyrene dopant is disclosed. However, a further improvement in luminous properties (luminous efficiency, lifetime or the like) has been desired.

RELATED ART DOCUMENTS

Patent Documents

Patent Document 1: WO2004/018587
Patent Document 2: JP-A-2004-204238
Patent Document 3: WO2005/108348

The invention has been made to solve the above-mentioned subject. An object of the invention is to provide a highly efficient and long-lived organic EL device.

The inventors have found that an organic light-emitting medium obtained by using a pyrene derivative having a specific structure at a specific position and a phenyl-substituted anthracene derivative has a high luminous efficiency and has a long life. The inventors have also found that an organic electroluminescence device using an organic thin film comprising the organic light-emitting medium as an emitting layer has a high luminous efficiency and has a long life. The invention has been made based on this finding.

According to the invention, the following organic light-emitting medium, organic thin film and organic electroluminescence device are provided.

1. An organic light-emitting medium comprising a pyrene derivative represented by the following formula (1) and a phenyl-substituted anthracene derivative represented by the following formula (2):

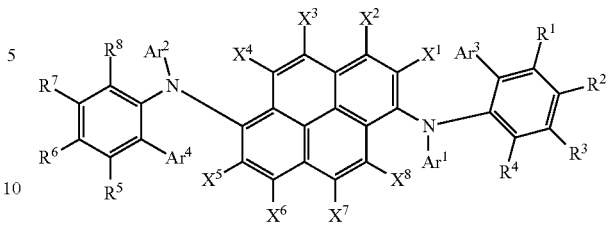

wherein
$Ar^1$ to $Ar^4$ are independently a substituted or unsubstituted aryl group having 6 to 30 carbon atoms that form a ring (hereinafter referred to as "ring carbon atoms"), or a substituted or unsubstituted heteroaryl group having 5 to 20 atoms that form a ring (hereinafter referred to as "ring atoms"), $X^1$ to $X^8$ are independently a hydrogen atom, a substituted or unsubstituted aryl group having 6 to 30 ring carbon atoms, a substituted or unsubstituted alkyl group having 1 to 20 carbon atoms, a substituted or unsubstituted cycloalkyl group having 3 to 20 ring carbon atoms, a silyl group which is substituted by a substituted or unsubstituted alkyl group having 1 to 20 carbon atoms and/or a substituted or unsubstituted aryl group having 6 to 18 ring carbon atoms, or which is unsubstituted, a cyano group, a substituted or unsubstituted alkoxy group having 1 to 20 carbon atoms, a substituted or unsubstituted aryloxy group having 6 to 30 ring carbon atoms, a substituted or unsubstituted aralkyl group having 6 to 30 ring carbon atoms, a halogen atom, or a substituted or unsubstituted halogenated alkyl group having 1 to 20 carbon atoms, $R^1$ to $R^8$ are independently a hydrogen atom, a substituted or unsubstituted aryl group having 6 to 30 ring carbon atoms, a substituted or unsubstituted alkyl group having 1 to 20 carbon atoms, a substituted or unsubstituted cycloalkyl group having 3 to 20 ring carbon atoms, a silyl group which is substituted by a substituted or unsubstituted alkyl group having 1 to 20 carbon atoms or a substituted or unsubstituted aryl group having 6 to 18 ring carbon atoms, or which is unsubstituted, a cyano group, a substituted or unsubstituted alkoxy group having 1 to 20 carbon atoms, a substituted or unsubstituted aryloxy group having 6 to 30 ring carbon atoms, or a substituted or unsubstituted aralkyl group having 6 to 30 ring carbon atoms, and $R^1$ and $R^2$, $R^2$ and $R^3$, $R^3$ and $R^4$, $R^5$ and $R^6$, $R^6$ and $R^7$, and $R^7$ and $R^8$ may be bonded to each other to form a substituted or unsubstituted hydrocarbon ring or a substituted or unsubstituted heterocyclic ring,

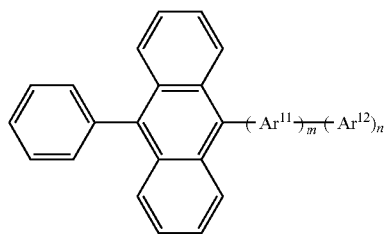

wherein

Ar$^{11}$ is a substituted or unsubstituted arylene group having 6 to 30 ring carbon atoms or a substituted or unsubstituted heteroarylene group having 5 to 20 ring atoms, m is an integer of 0 to 3, provided that Ar$^{11}$ is a single bond when m is 0, Ar$^{12}$ is a substituted or unsubstituted aryl group having 6 to 30 ring carbon atoms or a substituted or unsubstituted heteroaryl group having 5 to 20 ring atoms, n is an integer of 1 to 3, and when m or n is 2 or more, plural Ar$^{11}$s and Ar$^{12}$s may be the same or different.

2. The organic light-emitting medium according to 1, wherein X$^1$ to X$^8$ are a hydrogen atom.

3. The organic light-emitting medium according to 1, wherein X$^2$ and X$^6$ are a substituted or unsubstituted aryl group having 6 to 30 ring carbon atoms, a substituted or unsubstituted alkyl group having 1 to 20 carbon atoms or a substituted or unsubstituted cycloalkyl group having 3 to 20 ring carbon atoms, and X$^1$, X$^3$ to X$^5$, X$^7$ and X$^8$ are a hydrogen atom.

4. The organic light-emitting medium according to any one of 1 to 3, wherein Ar$^3$ and Ar$^4$ is a substituted or unsubstituted aryl group having 6 to 30 ring carbon atoms.

5. The organic light-emitting medium according to any of 1 to 4, wherein R$^3$ and R$^7$, or R$^2$ and R$^6$ are a substituted or unsubstituted aryl group having 6 to 30 ring carbon atoms.

6. The organic light-emitting medium according to 4 or 5, wherein Ar$^3$ and Ar$^4$ are a substituted or unsubstituted phenyl group.

7. The organic light-emitting medium according to 5 or 6, wherein R$^3$ and R$^7$, or R$^2$ and R$^6$ are a substituted or unsubstituted phenyl group.

8. The organic light-emitting medium according to any of 1 to 7, wherein m is 1 and n is 1.

9. The organic light-emitting medium according to any of 1 to 7, wherein m is 0 and n is 1.

10. The organic light-emitting medium according to 8, wherein Ar$^{11}$ is a substituted or unsubstituted arylene group having 6 to 18 ring carbon atoms or a substituted or unsubstituted heteroarylene group having 5 to 20 ring atoms, Ar$^{12}$ is a substituted or unsubstituted aryl group having 6 to 18 ring carbon atoms or a substituted or unsubstituted heteroaryl group having 5 to 20 ring atoms.

11. The organic light-emitting medium according to 9, wherein Ar$^{12}$ is a substituted or unsubstituted aryl group having 6 to 18 ring carbon atoms or a substituted or unsubstituted heteroaryl group having 5 to 20 ring atoms.

12. The organic light-emitting device according to 10, wherein Ar$^{11}$ is a substituted or unsubstituted phenylene group or a substituted or unsubstituted naphthalenylene group.

13. The organic light-emitting medium according to 11, wherein Ar$^{12}$ is a substituted or unsubstituted naphthyl group, a substituted or unsubstituted benzanthracenyl group, a substituted or unsubstituted benzphenanthrenyl group, a substituted or unsubstituted phenanthryl group or a substituted or unsubstituted dibenzofuranyl group.

14. The organic light-emitting medium according to 12, wherein Ar$^{11}$ is a substituted or unsubstituted phenylene group and Ar$^{12}$ is a substituted or unsubstituted naphthyl group.

15. A pyrene derivative represented by the following formula (10):

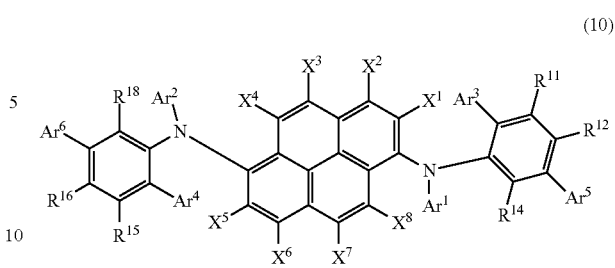

(10)

wherein

Ar$^1$ to Ar$^4$ are independently a substituted or unsubstituted aryl group having 6 to 30 ring carbon atoms, or a substituted or unsubstituted heteroaryl group having 5 to 20 ring atoms, X$^1$ to X$^8$ are independently a hydrogen atom, a substituted or unsubstituted aryl group having 6 to 30 ring carbon atoms, a substituted or unsubstituted alkyl group having 1 to 20 carbon atoms, a substituted or unsubstituted cycloalkyl group having 3 to 20 ring carbon atoms, a silyl group which is substituted by a substituted or unsubstituted alkyl group having 1 to 20 carbon atoms and/or a substituted or unsubstituted aryl group having 6 to 18 ring carbon atoms, or which is unsubstituted, a cyano group, a substituted or unsubstituted alkoxy group having 1 to 20 carbon atoms, a substituted or unsubstituted aryloxy group having 6 to 30 ring carbon atoms, a substituted or unsubstituted aralkyl group having 6 to 30 ring carbon atoms, a halogen atom, or a substituted or unsubstituted halogenated alkyl group having 1 to 20 carbon atoms, R$^{11}$, R$^{12}$, R$^{14}$ to R$^{16}$ and R$^{18}$ are independently a hydrogen atom, a substituted or unsubstituted alkyl group having 1 to 20 carbon atoms, a substituted or unsubstituted cycloalkyl group having 3 to 20 ring carbon atoms, a silyl group which is substituted by a substituted or unsubstituted alkyl group having 1 to 20 carbon atoms and/or a substituted or unsubstituted aryl group having 6 to 18 ring carbon atoms, or which is unsubstituted or a substituted or unsubstituted aralkyl group having 6 to 30 ring carbon atoms.

16. An organic electroluminescence medium comprising an anode and a cathode, and one or more organic thin film layers including an emitting layer between the anode and the cathode;

the emitting layer comprising the organic light-emitting device according to any of 1 to 14 or the pyrene derivative according to 15.

According to the invention, an organic light-emitting medium, an organic thin film and an organic EL device with a high efficiency and long life can be provided.

MODE FOR CARRYING OUT THE INVENTION

The organic emission medium and the organic EL device of the invention will be described in detail hereinbelow.

I. Organic Emission Medium

The organic emission medium of the invention is characterized in that it comprises a pyrene derivative represented by the following formula (1) and a phenyl-substituted anthracene derivative represented by the following formula (2).

Here, the pyrene derivative represented by the formula (1) functions as a doping material (dopant), and the phenyl-substituted anthracene derivative represented by the following formula (2) functions as a host material.

(1)

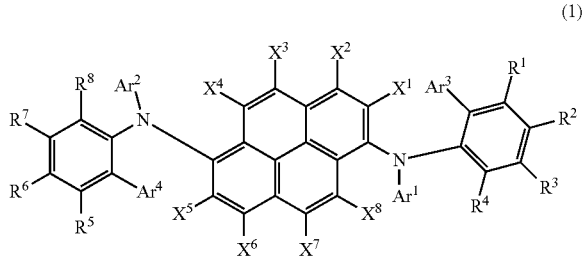

wherein $Ar^1$ to $Ar^4$ are independently a substituted or unsubstituted aryl group having 6 to 30 atoms that form a ring (hereinafter referred to as the "ring carbon atoms") or a substituted or unsubstituted heteroaryl group having 5 to 20 atoms that form a ring (hereinafter the "ring atoms");

$X^1$ to $X^8$ are independently a hydrogen atom, a substituted or unsubstituted aryl group having 6 to 30 ring carbon atoms, a substituted or unsubstituted alkyl group having 1 to 20 carbon atoms, a substituted or unsubstituted cycloalkyl group having 3 to 20 ring carbon atoms, a silyl group which is substituted by a substituted or unsubstituted alkyl group having 1 to 20 carbon atoms and/or a substituted or unsubstituted aryl group having 6 to 18 ring carbon atoms, or which is unsubstituted, a cyano group, an alkoxy group having 1 to 20 carbon atoms, a substituted or unsubstituted aryloxy group having 6 to 30 ring carbon atoms, a substituted or unsubstituted aralkyl group having 6 to 30 ring carbon atoms, a halogen atom or a substituted or unsubstituted halogenated alkyl group having 1 to 20 carbon atoms;

$R^1$ to $R^8$ are independently a hydrogen atom, a substituted or unsubstituted aryl group having 6 to 30 ring carbon atoms, a substituted or unsubstituted alkyl group having 1 to 20 carbon atoms, a substituted or unsubstituted cycloalkyl group having 3 to 20 ring carbon atoms, a silyl group which is substituted by a substituted or unsubstituted alkyl group having 1 to 20 carbon atoms and/or a substituted or unsubstituted aryl group having 6 to 18 ring carbon atoms, or which is unsubstituted, a cyano group, a substituted or unsubstituted alkoxy group having 1 to 20 carbon atoms, a substituted or unsubstituted aryloxy group having 6 to 30 ring carbon atom or a substituted or unsubstituted aralkyl group having 6 to 30 ring carbon atoms, and $R^1$ and $R^2$, $R^2$ and $R^3$, $R^3$ and $R^4$, $R^5$ and $R^6$, $R^6$ and $R^7$ and $R^7$ and $R^8$ may be bonded with each other to form a substituted or unsubstituted hydrocarbon ring or a substituted or unsubstituted heterocyclic ring.

(2)

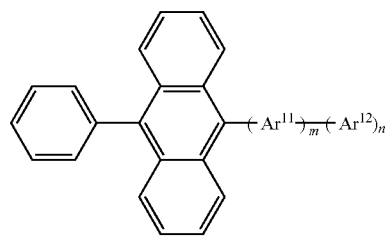

wherein $Ar^{11}$ is a substituted or unsubstituted arylene group (aromatic hydrocarbon group) having 6 to 30 ring carbon atoms or a substituted or unsubstituted heteroarylene group (aromatic heterocyclic group) having 5 to 20 ring atoms, m is an integer of 0 to 3, and when m is 0, $Ar^{11}$ is a single bond, $Ar^{12}$ is a substituted or unsubstituted aryl group having 6 to 30 ring carbon atoms or a substituted or unsubstituted heteroaryl group having 5 to 20 ring atoms, n is an integer of 1 to 3; and when m or n is 2 or more, plural $Ar^{11}$s and $Ar^{12}$s may be the same or different.

Hereinbelow, each substituent in the formulas (1) and (2) will be explained with reference to the specific examples, or the like.

In this specification, the "carbon atoms that form a ring" means carbon atoms that constitute a saturated aliphatic cyclic structure, an unsaturated aliphatic cyclic structure or an aromatic hydrocarbon cyclic structure which are each composed of carbon and hydrogen. The "atoms that form a ring" means carbon atoms and hetero atoms that constitute a saturated aliphatic cyclic structure, an unsaturated aliphatic cyclic structure and an aromatic heterocyclic structure each containing a hetero atom.

The "hydrocarbon ring" includes a saturated aliphatic cyclic structure, an unsaturated aliphatic cyclic structure or an aromatic hydrocarbon cyclic structure which are each composed of carbon and hydrogen, and the "heterocyclic ring" includes a saturated aliphatic cyclic structure, an unsaturated aliphatic cyclic structure and an aromatic heterocyclic structure each containing a hetero atom.

In this specification, all atoms constituting the pyrene derivative represented by the formula (1) and the phenyl-substituted anthracene derivative represented by the formula (2) include corresponding isotopes.

The aryl group having 6 to 30 ring carbon atoms represented by $Ar^1$ to $Ar^4$, $X^1$ to $X^8$ and $R^1$ to $R^8$ and $Ar^{12}$ includes a non-fused aromatic hydrocarbon ring group having 6 to 30 ring carbon atoms, a fused aromatic hydrocarbon ring group having 10 to 30 ring carbon atoms and a ring-assembling aromatic hydrocarbon ring group having 9 to 30 ring carbon atoms. Here, the "non-fused aromatic hydrocarbon ring group" means a group in which a plurality of aromatic rings (a monocyclic ring and/or a fused ring) is bonded by a single bond. The "fused aromatic hydrocarbon ring group" means a ring in which a plurality of aromatic rings are bonded by two or more common ring carbon atoms. The "ring-assembling aromatic hydrocarbon ring group" means a ring in which an aromatic ring and an aliphatic ring are bonded by two or more common carbon ring atoms.

Specific examples of the aryl group having 6 to 30 ring carbon atoms include a phenyl group, a naphthyl group, an anthryl group, a phenanthryl group, a naphthacenyl group, a pyrenyl group, a crysenyl group, a fluorenyl group, a benzo[c]phenanthryl group, a benzo[g]chrysenyl group, a triphenylenyl group, a 9,9-dimethylfluorenyl group, a benzofluorenyl group, a dibenzofluorenyl group, a biphenylyl group, a terphenylyl group and a fluoranthenyl group. Of the above-mentioned aryl groups, a phenyl group, a biphenylyl group, a tolyl group, a xylyl group and a naphthyl group are particularly preferable. It is preferred that the aryl group have 6 to 18 ring carbon atoms, more preferably 6 to 10 ring carbon atoms.

The heteroaryl group having 5 to 20 ring atoms represented by $Ar^1$ to $Ar^4$ and $Ar^{12}$ includes, a non-fused aromatic heterocyclic group having 5 to 20 ring atoms, and a fused aromatic heterocyclic group having 10 to 20 ring atoms and a ring-assembling aromatic heterocyclic group having 9 to 20 ring atoms. Here, the "non-fused aromatic heterocyclic group" means a group in which two or more aromatic rings including one or more aromatic heterocyclic rings (a monocyclic ring and/or a fused ring) are bonded by a single bond. The "fused aromatic heterocyclic group" means a ring in which two or more aromatic rings including one or more aromatic heterocyclic rings are bonded by two or more common ring atoms. The "ring-assembling aromatic heterocyclic group" means a ring in which one or more aromatic rings and one or more aliphatic rings are bonded by two or more common carbon atoms.

Specific examples of the heteroaryl group having 5 to 20 ring atoms include a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalynyl group, a carbazolyl group, a phenanthrydinyl group, an acridinyl group, a phenanthronyl group, a phenazinyl group, a phenothiazinyl group, a phenoxazinyl group, an oxazolyl group, an oxadiazolyl group, a frazanyl group, a thienyl group, a 2-methylpyrrolyl group, a triazinyl group, a pyrimidinyl group or the like. Of these, a dibenzofuranyl group, a dibenzothiophenyl group and a carbazolyl group are preferable. It is preferred that the heteroaryl group have 5 to 14 ring atoms.

As the alkyl group having 1 to 20 carbon atoms represented by $X^1$ to $X^8$ and $R^1$ to $R^8$, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group or the like can be given. Of these, a methyl group, an ethyl group, a propyl group, an isopropyl group, an n-butyl group, an s-butyl group, an isobutyl group, a t-butyl group, an n-pentyl group and an n-hexyl group are preferable. The number of carbon atoms is preferably 1 to 10, more preferably 1 to 8, with 1 to 6 being further preferable.

As the cycloalkyl group having 3 to 20 ring carbon atoms represented by $X^1$ to $X^8$ and $R^1$ to $R^8$, a cyclopropyl group, a cyclobutyl group, a cyclopentyl group, a cyclohexyl group, a 1-adamantyl group, a 2-adamantyl group, a 1-norbornyl group, a 2-norbornyl group or the like can be given. The number of ring carbon atoms is preferably 3 to 10, more preferably 3 to 8, with 3 to 6 being further preferable.

As the silyl group substituted by a substituted or unsubstituted alkyl group having 1 to 20 carbon atoms and/or a substituted or unsubstituted aryl group having 6 to 18 ring carbon atoms or unsubstituted represented by $X^1$ to $X^8$ and $R^1$ to $R^8$, the following can be given.

The alkyl-substituted silyl group is represented by —$SiY_3$, and examples of Y include the examples of the alkyl group having 1 to 20 carbon atoms. Specific examples include a trimethylsilyl group, a triethylsilyl group, a t-butyldimethylsilyl group, a propyldimethylsilyl group or the like can be given.

The aryl-substituted silyl group is represented by —$SiZ_3$, and examples of Z include aryl groups having 6 to 18 ring carbon atoms of the above-mentioned examples of the aryl groups having 6 to 30 ring carbon atoms. Specific examples include a triphenylsilyl group, a phenydimethylsilyl group, a t-butyldiphenylsilyl group, a tritolylsilyl group, a trixylylsilyl group or the like can be given.

The alkyl- and aryl-substituted silyl group is represented by —$SiY_nZ_{(3-n)}$ (n is 1 or 2). As examples of Y, the above examples of the alkyl group having 1 to 20 carbon atoms can be given. As examples of Z, of the above examples of the aryl group having 6 to 30 ring carbon atoms, aryl groups having 6 to 18 ring carbon atoms can be given.

The alkoxy group having 1 to 20 carbon atoms represented by $X^1$ to $X^8$ and $R^1$ to $R^8$ is represented by —OY. Examples of Y include examples of the alkyl group having 1 to 20 carbon atoms. Specific examples include a methoxy group, an ethoxy group, a butoxy group or the like.

The aryloxy group having 6 to 30 ring carbon atoms represented by $X^1$ to $X^8$ and $R^1$ to $R^8$ is represented by —OZ, and examples of Z include the above-mentioned examples of the aryl group having 6 to 30 ring carbon atoms. Specific examples include a phenoxy group or the like.

The aralkyl group having 6 to 30 ring carbon atoms represented by $X^1$ to $X^8$ and $R^1$ to $R^8$ is represented by —Y—Z, and examples of Y include examples of the alkylene group corresponding to the above-mentioned examples of the alkyl group having 1 to 20 carbon atoms. As examples of Z, the above-mentioned examples of the aryl group having 6 to 30 ring carbon atoms can be given. Specific examples include a benzyl group, a phenylethyl group, a 2-phenylpropane-2-yl group or the like can be given.

As the halogen atom represented by $X^1$ to $X^8$, fluorine, chlorine, bromine, iodine or the like can be given. A fluorine atom is preferable.

As the halogenated alkyl group having 1 to 20 carbon atoms represented by $X^1$ to $X^8$, fluoroalkyl having 1 to 20 carbon atoms is preferable. Specifically, a fluoromethyl group, a difluoromethyl group, a trifluoromethyl group, a fluoroethyl group, a trifluoromethylmethyl group or the like can be given.

The arylene group having 6 to 30 ring carbon atoms represented by $Ar^{11}$ is represented by —Z—, and as examples of Z, the arylene group corresponding to the above-mentioned examples of the aryl group having 6 to 30 ring carbon atoms can be given.

The heteroarylene group having 5 to 20 ring atoms represented by $Ar^{11}$ is represented by —P—, and as examples of P, a heteroarylene group corresponding to the above-mentioned examples of the heteroaryl group having 5 to 20 ring atoms can be given.

As the substituent of the above-mentioned each "substituted or unsubstituted" group, an alkyl group having 1 to 20 carbon atoms, a silyl group substituted by an alkyl group having 1 to 20 carbon atoms and/or an aryl group having 6 to 18 ring carbon atoms, an alkoxy group having 1 to 20 carbon atoms, a haloalkyl group having 1 to 20 carbon atoms, a haloalkoxy group having 1 to 20 carbon atoms, an aryl group having 6 to 30 ring carbon atoms, a heteroaryl group having 5 to 20 ring atoms, an aryloxy group having 6 to 30 ring carbon atoms, an aralkyl group having 6 to 30 ring carbon atoms, a cycloalkyl group having 3 to 20 carbon atoms, a cyano group, a carboxy group, a carbonyl compound having 1 to 20 carbon atoms, a fluorine atom, a halogenated alkyl having 1 to 20 carbon atoms or the like can be given.

In the above formula (1), $R^1$ and $R^2$, $R^2$ and $R^3$, $R^3$ and $R^4$, $R^5$ and $R^6$, $R^6$ and $R^7$, $R^7$ and $R^8$ may be bonded with each other to form a substituted or unsubstituted hydrocarbon ring or a substituted or unsubstituted heterocyclic ring. Specific hydrocarbon rings include a naphthyl group, a phenanthryl group, a pyrenyl group, a 9,9-dimethylfluorenyl group or the like. Specific examples of the formed heterocyclic ring include a benzofuranyl group, a dibenzofuranyl group, a benzothienyl group, a dibenzothienyl group, a 1-arylindolyl group, a 9-arylcarbazolyl group or the like can be given.

In the formula (2), m is a repeating number of $Ar^{11}$, which is an integer of 0 to 3, preferably 0 to 2. When m is 2 or more, plural $Ar^{11}$s may be the same or different. If m is 0, $Ar^{11}$ is a single bond.

In the formula (2), when m is 1 to 3, n is the number of substitution of $Ar^{12}$ to $Ar^{11}$, which is an integer of 1 to 3, preferably an integer of 1 to 2. When n is 2 or more, plural $Ar^{12}$s may be the same or different. When m is 0, n is 1, and $Ar^{12}$ is bonded to the anthracene skeleton.

It is preferred that, in the formula (1), $X^2$ be a substituted or unsubstituted alkyl group having 1 to 20 carbon atoms, a substituted or unsubstituted cycloalkyl group having 3 to 10 ring carbon atoms, a silyl group which is substituted by a substituted or unsubstituted alkyl group having 1 to 20 carbon atoms and/or a substituted or unsubstituted aryl group having 6 to 18 ring carbon atoms, or unsubstituted, or a substituted or unsubstituted aryl group having 6 to 30 ring carbon atoms; and $X^1$ and $X^3$ to $X^8$ are hydrogen atoms.

In another preferred embodiment, in the formula (1), $X^2$ and $X^6$ are a substituted or unsubstituted alkyl group having 1 to 20 carbon atoms, a substituted or unsubstituted cycloalkyl group having 3 to 10 ring carbon atoms, a silyl group which is substituted by a substituted or unsubstituted alkyl group having 1 to 20 carbon atoms and/or a substituted or unsubstituted aryl group having 6 to 18 ring carbon atoms, or which is unsubstituted, or a substituted or unsubstituted aryl group having 6 to 30 ring carbon atoms, and $X^1$, $X^3$, $X^4$, $X^5$, $X^7$ and $X^8$ are hydrogen atoms.

The substituted or unsubstituted alkyl group having 1 to 20 carbon atoms represented by $X^2$ and $X^6$ is preferably an alkyl group having 1 to 6 carbon atoms. The silyl group substituted by a substituted or unsubstituted alkyl group having 1 to 20 carbon atoms and/or substituted or unsubstituted aryl group having 6 to 18 ring carbon atoms represented by $X^2$ and $X^6$, or unsubstituted is preferably a substituted or unsubstituted alkylsilyl group having 3 to 20 carbon atoms, and more preferably an alkylsilyl group having 3 to 12 carbon atoms.

In another preferable embodiment, in the formula (1), $X^1$ to $X^8$ are hydrogen atoms.

In the formula (1), it is preferred that $X^2$ and $X^6$ be a substituted or unsubstituted aryl group having 6 to 30 ring carbon atoms, a substituted or unsubstituted alkyl group having 1 to 20 carbon atoms or a substituted or unsubstituted cycloalkyl group having 3 to 20 ring carbon atoms, and $X^1$, $X^3$ to $X^5$ and $X^7$ and $X^8$ are hydrogen atoms.

It is preferred that, in the formula (1), $Ar^3$ and $Ar^4$ are a substituted or unsubstituted aryl group having 6 to 30 ring carbon atoms.

It is preferred that, in the formula (1), $R^3$ and $R^7$, or $R^2$ and $R^6$, be a substituted or unsubstituted aryl group having 6 to 30 ring carbon atoms. In this case, it is preferred that the remaining $R^1$ to $R^8$ are hydrogen.

It is preferred that, in the formula (1), $Ar^3$ and $Ar^4$ be a substituted or unsubstituted phenyl group.

In the formula (1), it is preferred that $R^3$ and $R^7$ or $R^2$ and $R^6$ be a substituted or unsubstituted phenyl group. In this case, it is preferred that the remaining $R^1$ to $R^8$ are hydrogen.

From the viewpoint of easiness in synthesis, in the formula (1), it is preferred that at least one or more, more preferably all of $Ar^1$ and $Ar^2$, $Ar^3$ and $Ar^4$, $R^1$ and $R^5$, $R^2$ and $R^6$, $R^3$ and $R^7$, $R^4$ and $R^8$, $X^1$ and $X^5$, $X^2$ and $X^6$, $X^3$ and $X^7$ and $X^4$ and $X^8$ be the same (point symmetrical).

It is preferred that, in the formula (2), m be 1 and n be 1.

In this case, it is preferred that $Ar^{11}$ be a substituted or unsubstituted arylene group having 6 to 18 ring carbon atoms or a substituted or unsubstituted heteroarylene group having 5 to 20 ring atoms, and $Ar^{12}$ be a substituted or unsubstituted aryl group having 6 to 18 ring carbon atoms or a substituted or unsubstituted heteroaryl group having 5 to 20 ring atoms.

It is more preferred that $Ar^{11}$ be a substituted or unsubstituted phenylene group or a substituted or unsubstituted naphthalene group.

It is further preferred that $Ar^{11}$ be a substituted or unsubstituted phenylene group and $Ar^{12}$ be a substituted or unsubstituted naphthyl group.

In the formula (2), it is preferred that m be 0 and n be 1.

In this case, it is preferred that $Ar^{12}$ be a substituted or unsubstituted aryl group having 6 to 18 ring carbon atoms or a substituted or unsubstituted heteroaryl group having 5 to 20 ring atoms.

Further, it is more preferred that $Ar^{12}$ be a substituted or unsubstituted naphthyl group, a substituted or unsubstituted benzanthracenyl group, a substituted or unsubstituted benzophenanthrenyl group, a substituted or unsubstituted phenanthryl group or a substituted or unsubstituted dibenzofuranyl group.

Specific preferable compounds of the pyrene derivative represented by the formula (1) used in the organic light-emitting medium of the invention are given below.

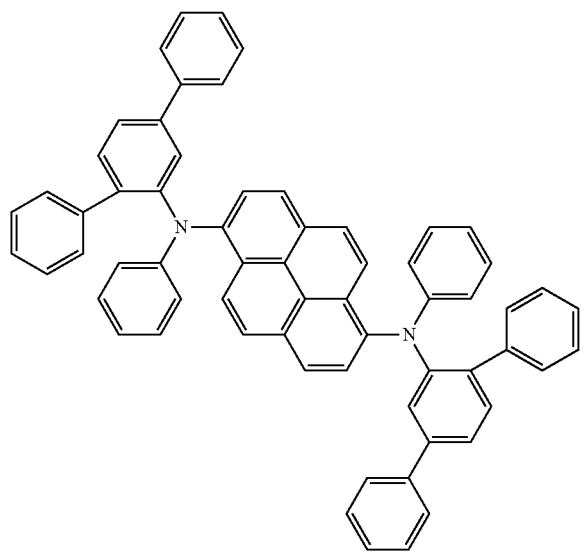

D-1

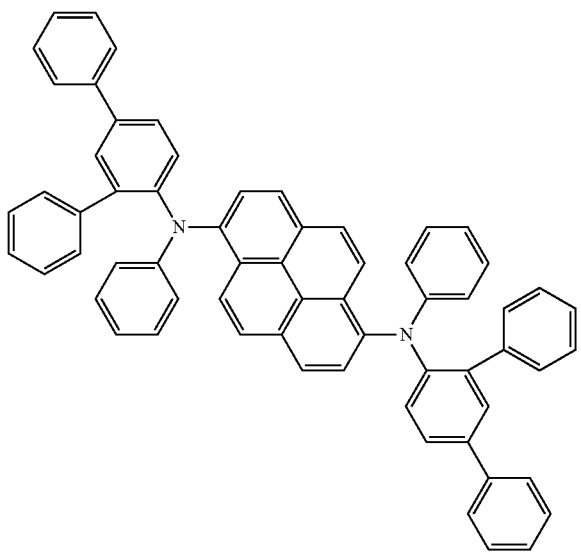

D-2

-continued
D-3
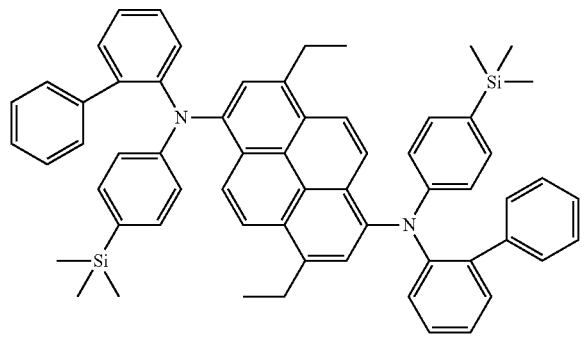
D-4
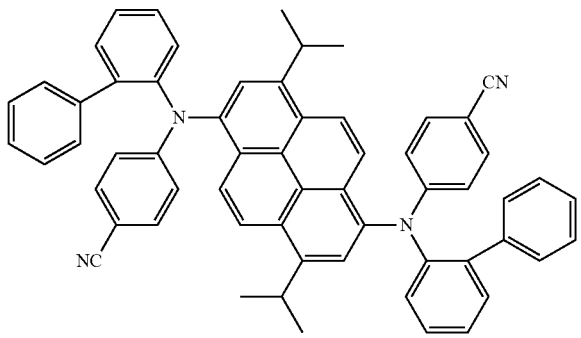
D-5
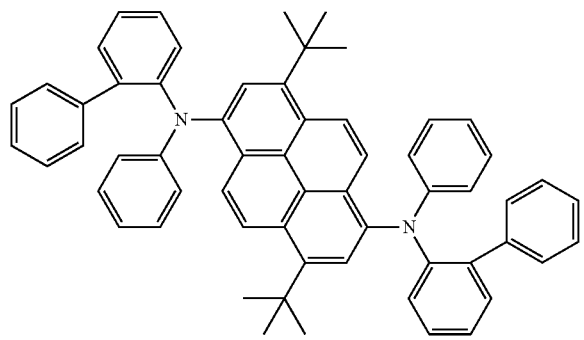
D-6
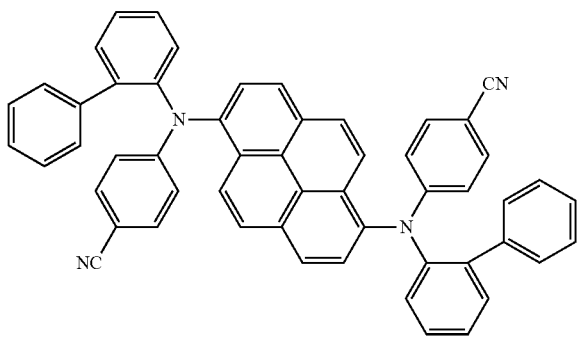
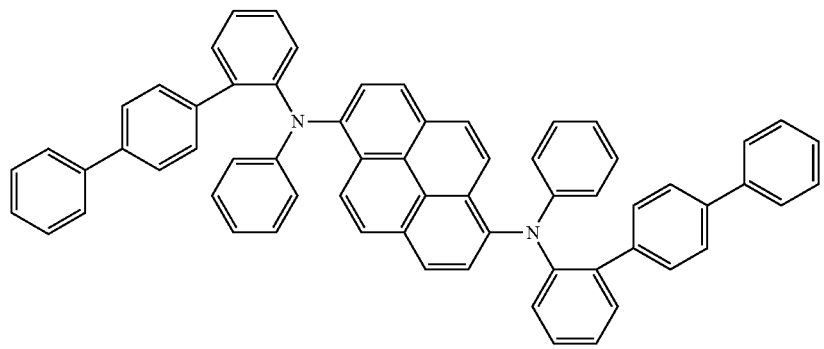
D-7
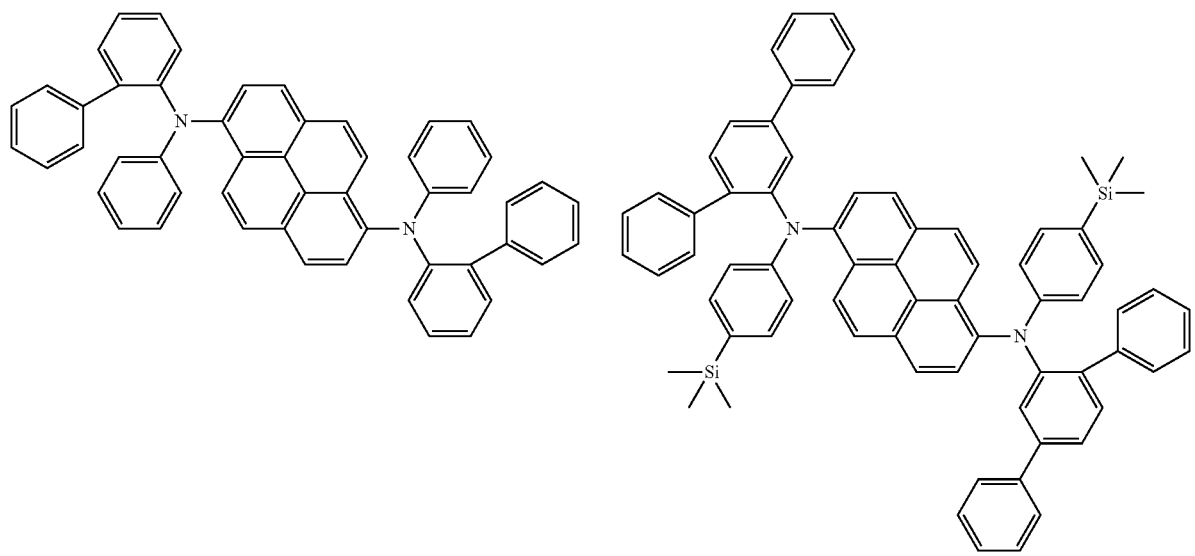

-continued
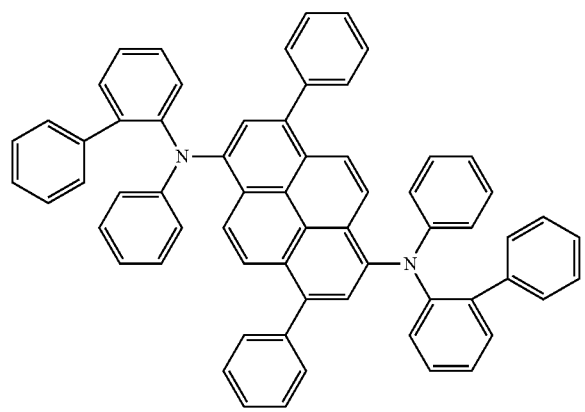
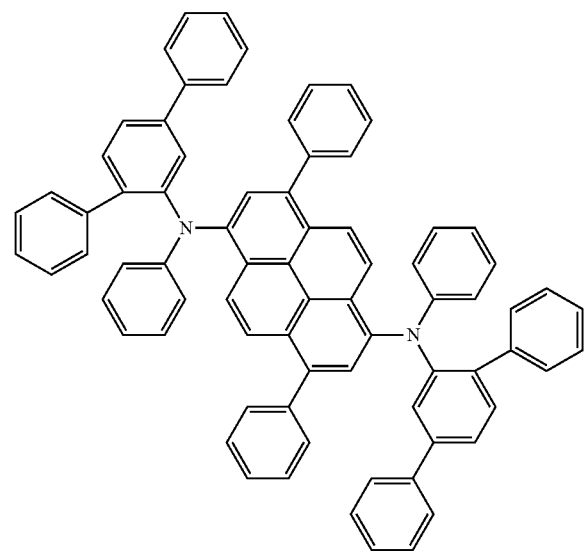
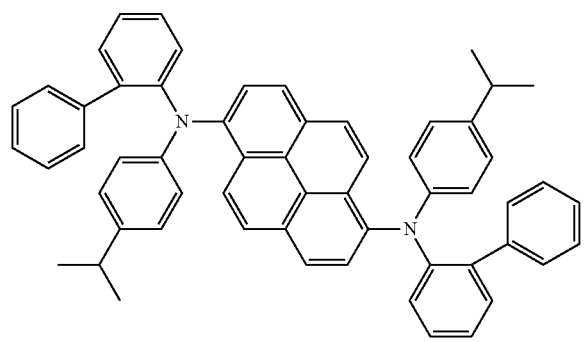
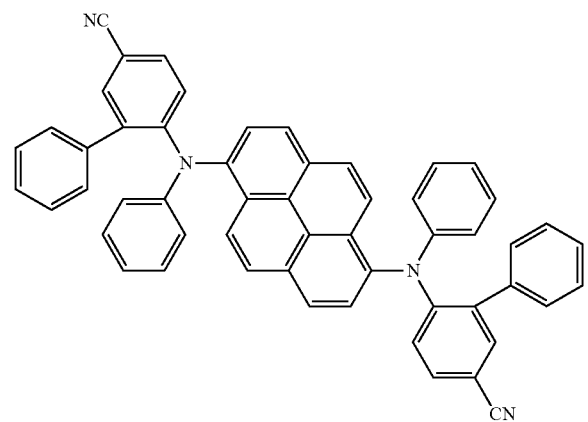
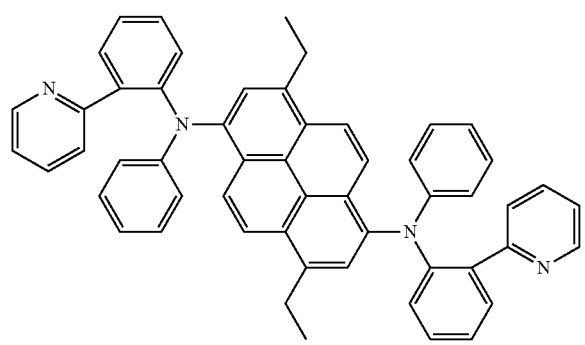
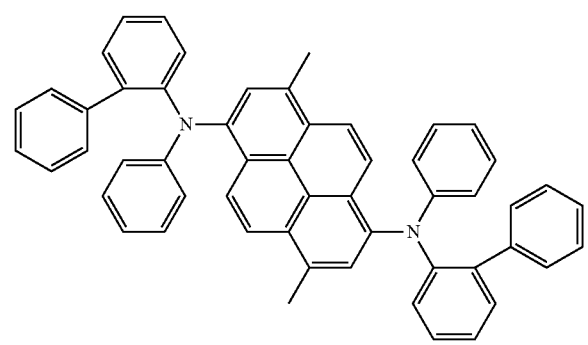

-continued
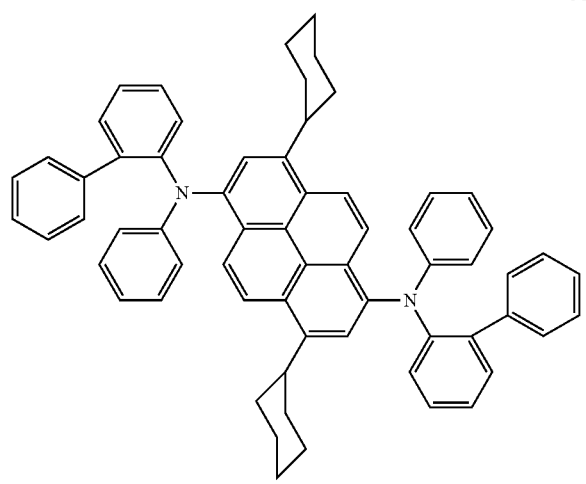
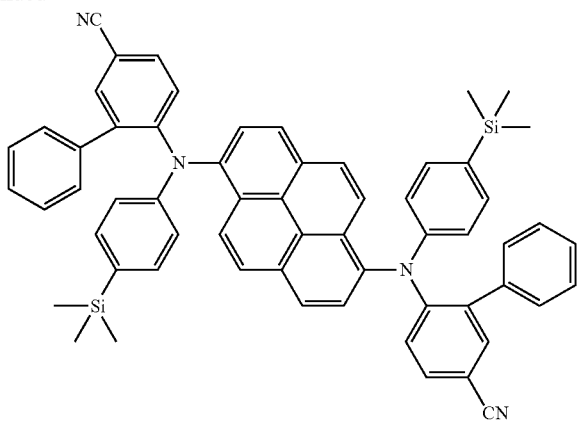
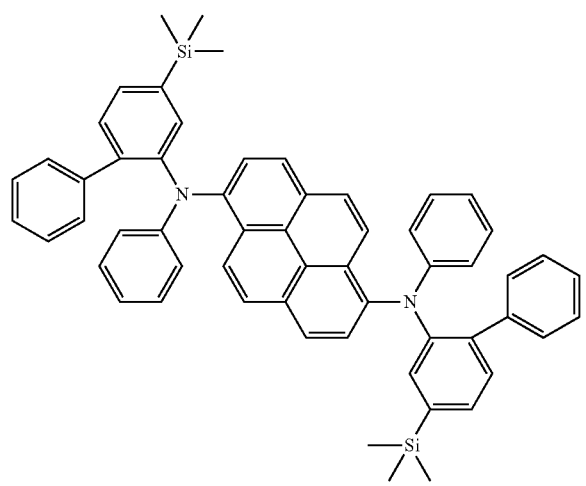
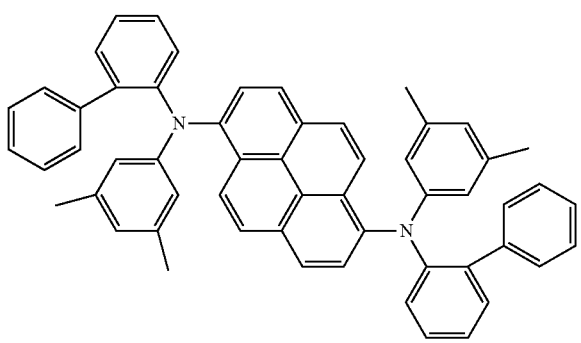
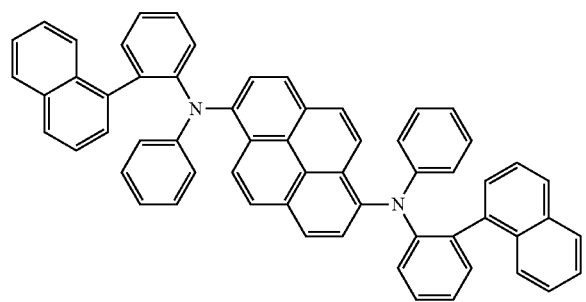
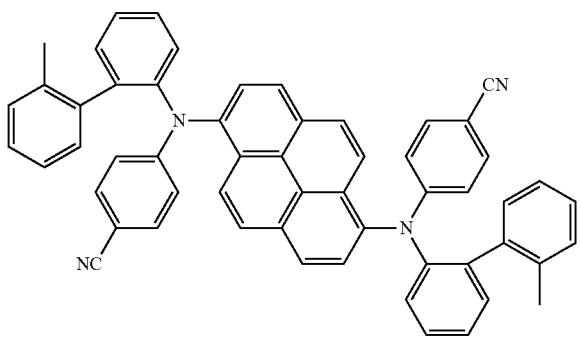
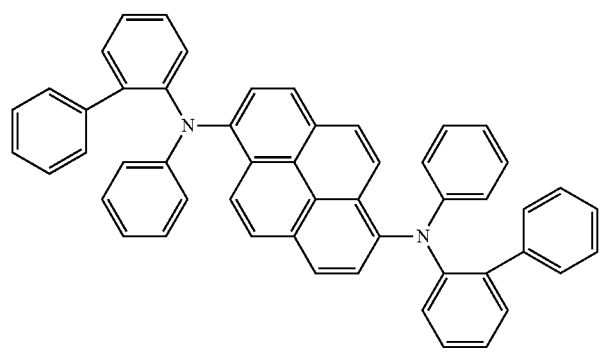

-continued
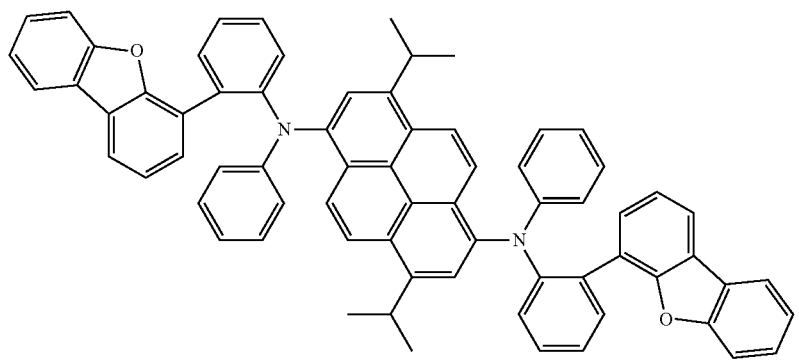
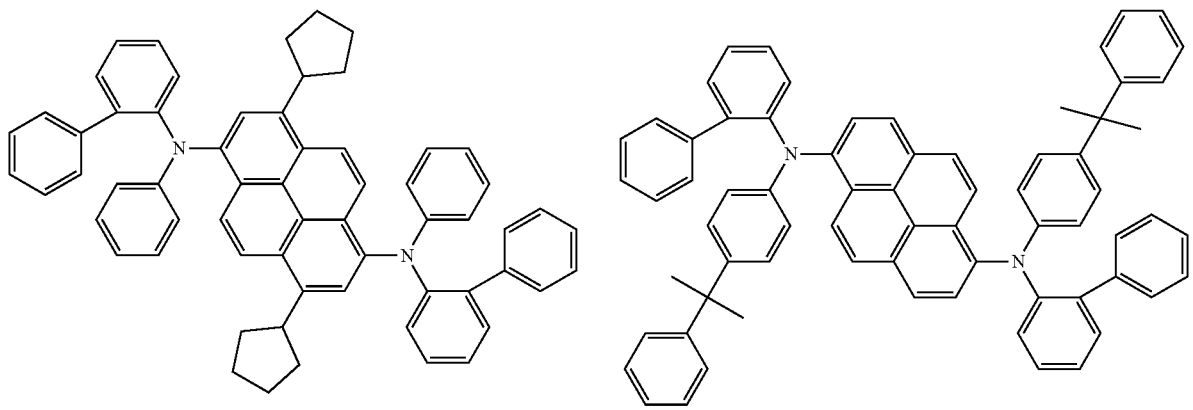
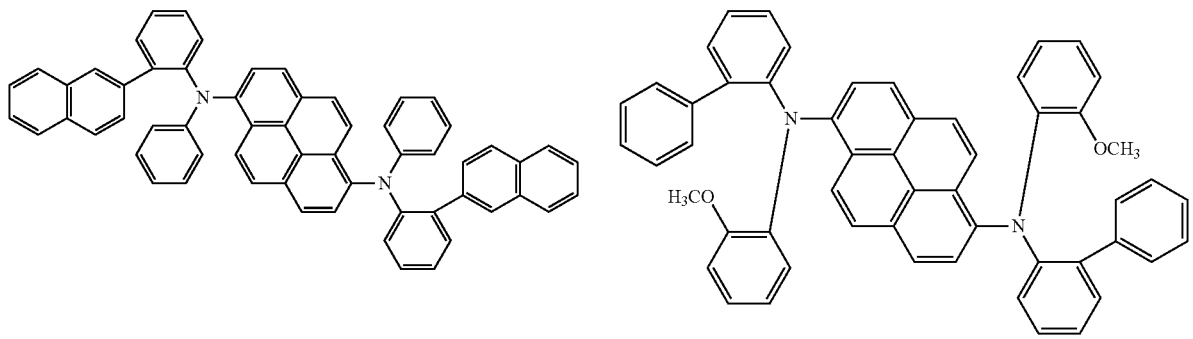
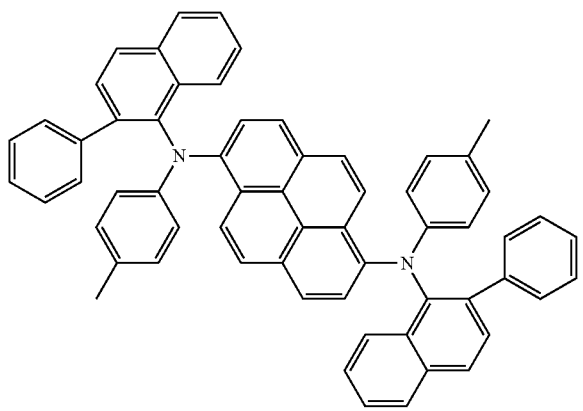

-continued
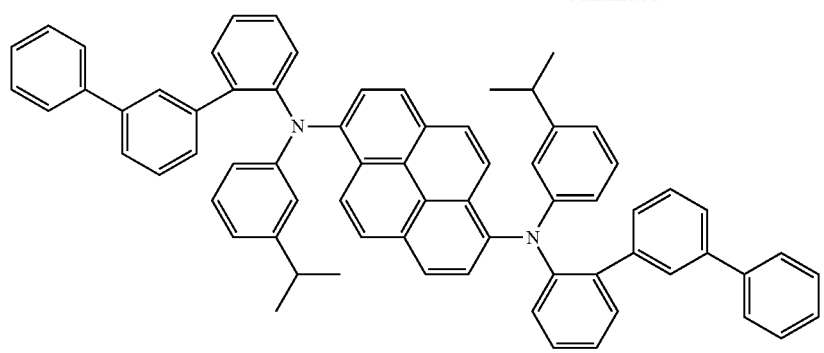
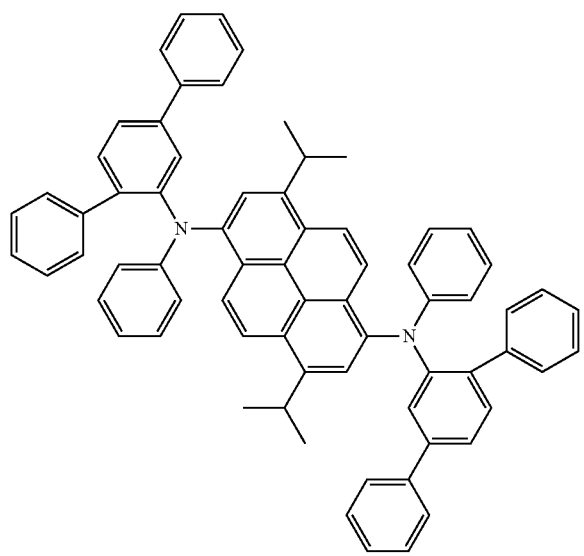
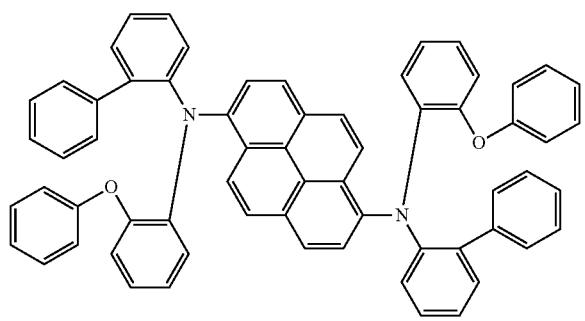
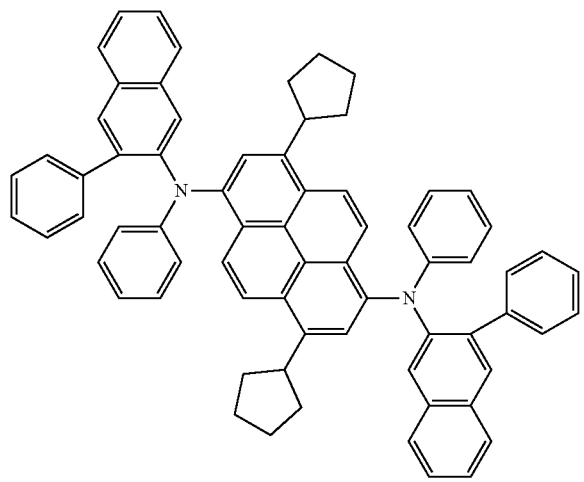
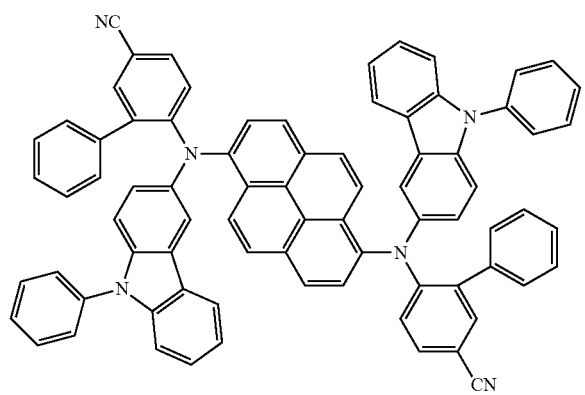

-continued
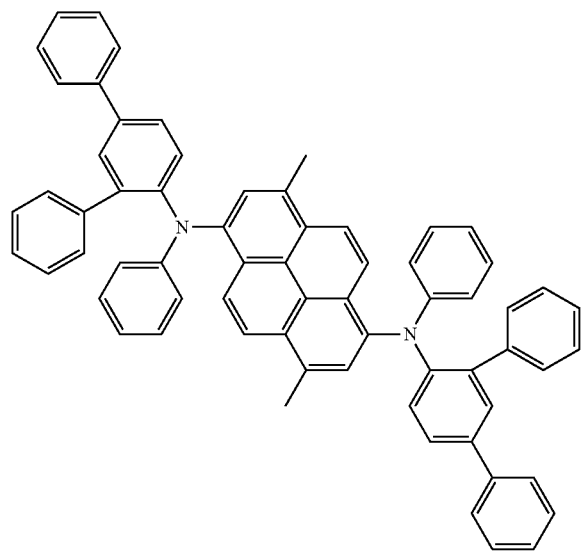
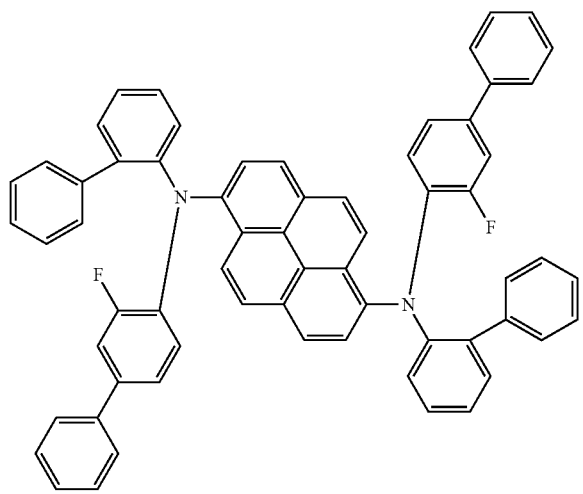
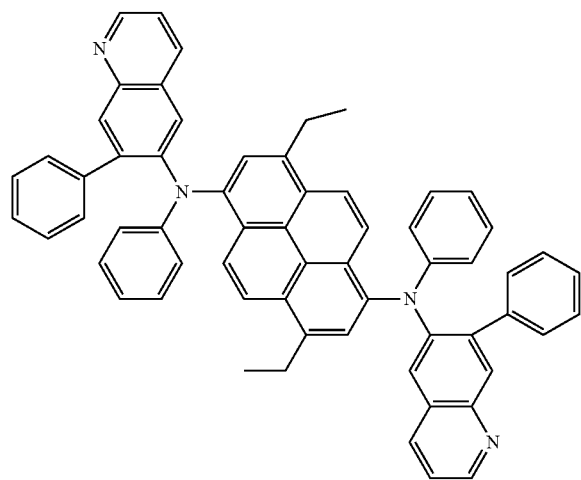
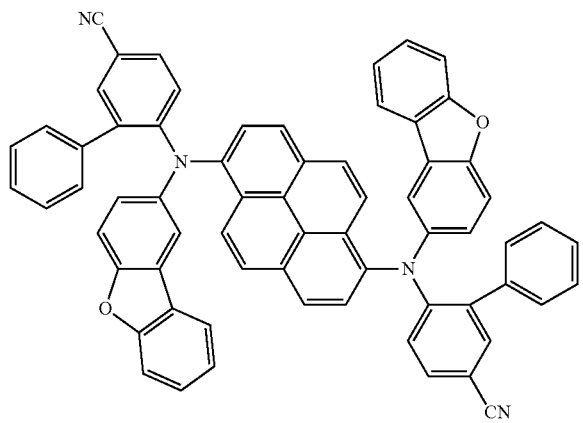
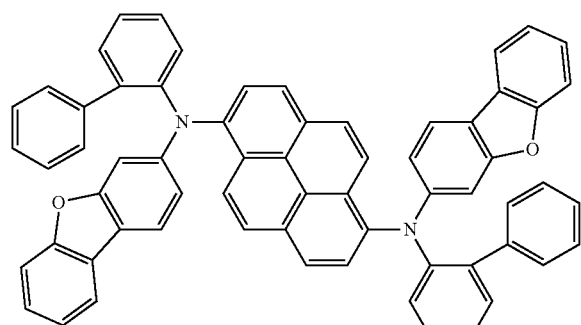
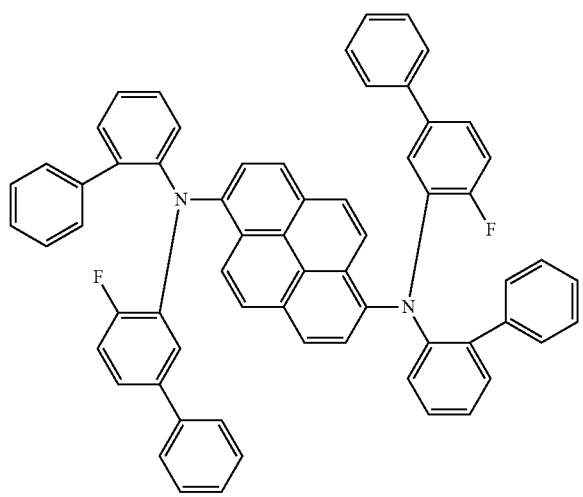

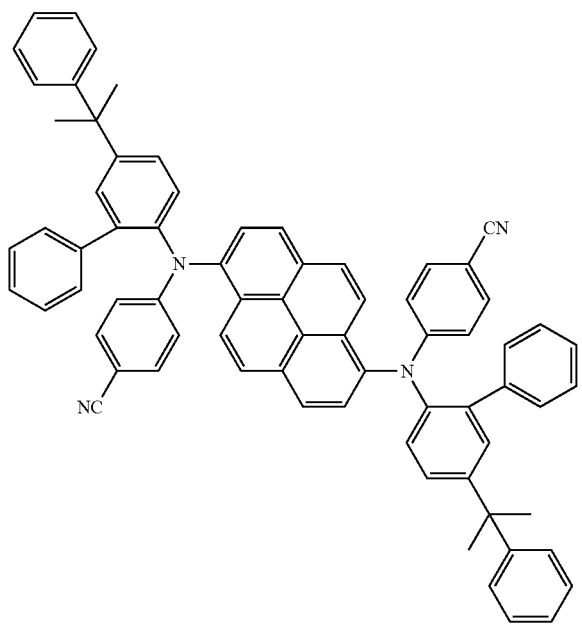
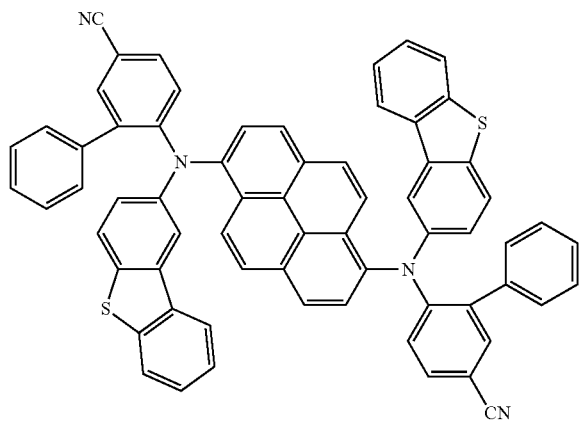
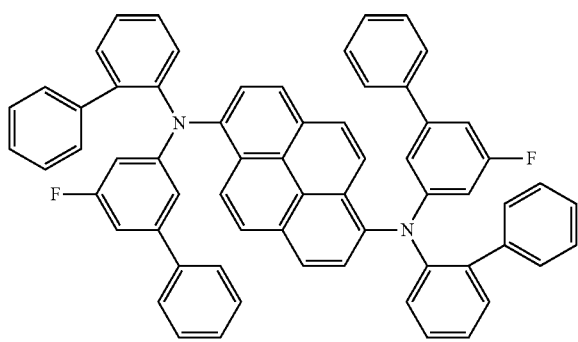
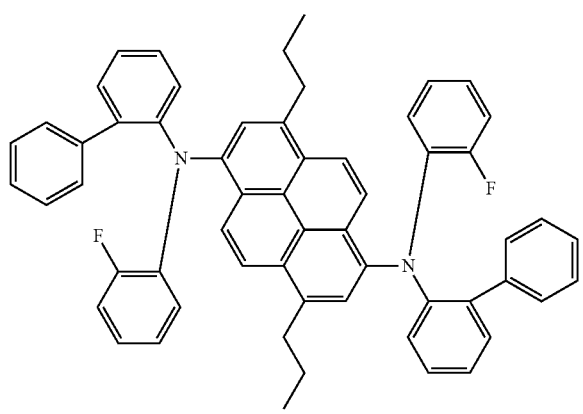
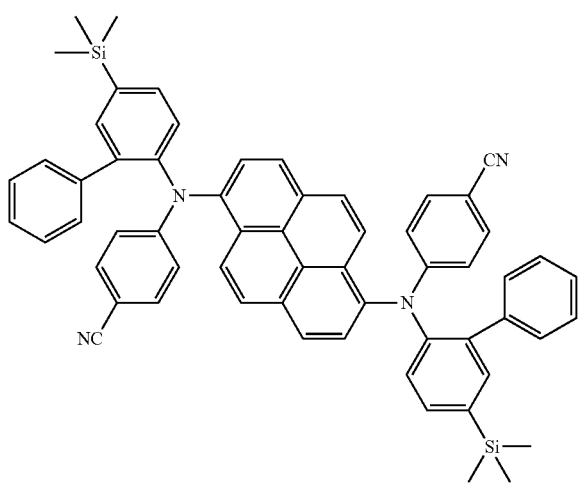
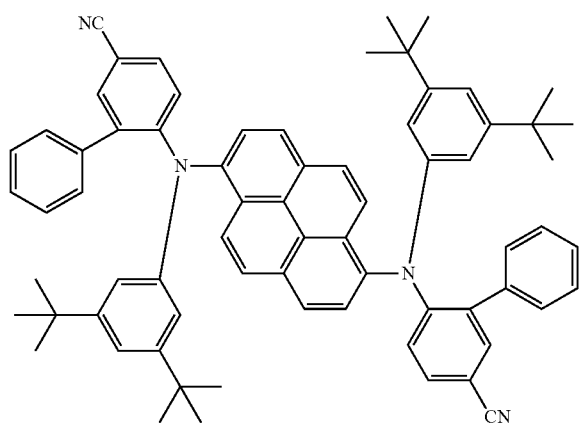

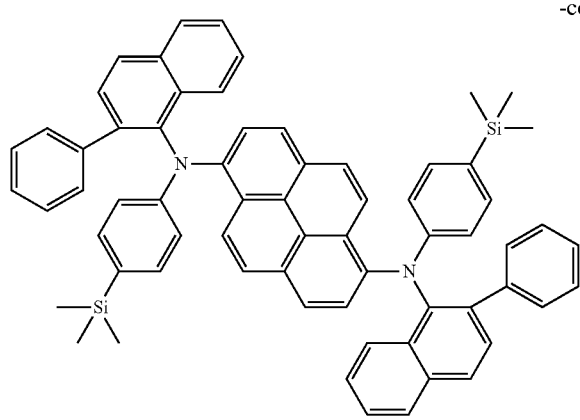

The invention further provides the compound represented by the following formula (10). In the organic light-emitting medium, together with the derivative of the formula (2), the compound represented by the formula (10) can be used. In this case, the derivative represented by the formula (2) and the compound represented by the formula (10) function as the host material and the dopant material, respectively.

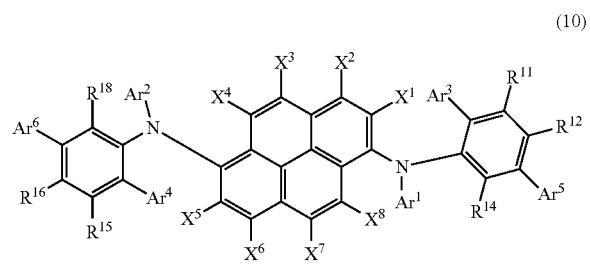

In the formula (10), $Ar^1$ to $Ar^4$ and $X^1$ to $X^8$ are the same as $Ar^1$ to $Ar^4$ and $X^1$ to $X^8$ in the formula (1), respectively, and an explanation thereof is omitted.

$Ar^5$ and $Ar^6$ are the same as $Ar^1$ to $Ar^4$ in the formula (1), and an explanation thereof is omitted.

$R^{11}$, $R^{12}$, $R^{14}$ to $R^{16}$ and $R^{18}$ are independently a hydrogen atom, a substituted or unsubstituted alkyl group having 1 to 20 carbon atoms, a substituted or unsubstituted cycloalkyl group having 3 to 20 ring carbon atoms, a silyl group which is substituted by a substituted or unsubstituted alkyl group having 1 to 20 carbon atoms and/or a substituted or unsubstituted aryl group having 6 to 18 ring carbon atoms, or which is unsubstituted, or a substituted or unsubstituted aralkyl group having 6 to 30 ring carbon atoms.

The alkyl group having 1 to 20 carbon atoms, the cycloalkyl group having 3 to 20 ring carbon atoms, the silyl group which is substituted by a substituted or unsubstituted alkyl group having 1 to 20 carbon atoms and/or a substituted or unsubstituted aryl group having 6 to 18 ring carbon atoms, or which is unsubstituted, or a substituted or unsubstituted aralkyl group having 6 to 30 ring carbon atoms represented by $R^{11}$, $R^{12}$, $R^{14}$ to $R^{16}$ and $R^{18}$, and the substituents substituting these groups are respectively the same as the corresponding groups in the formula (1) and the substituents thereof, and an explanation thereof is omitted.

In the explanation of preferred examples of the derivative in the formula (1), the explanation for $Ar^1$ to $Ar^4$ and $X^1$ to $X^8$ also applies to the derivatives of the formula (10).

It is preferred that $Ar^5$ and $Ar^6$ be a substituted or unsubstituted aryl group having 6 to 30 ring carbon atoms, with a substituted or unsubstituted phenyl group being more preferable.

As for $R^{11}$, $R^{12}$, $R^{14}$ to $R^{16}$ and $R^{18}$, they are preferably hydrogen.

Further, it is preferred that $R^{12}$ and $R^{16}$ be a substituted or unsubstituted aryl group having 6 to 30 ring carbon atoms, with a substituted or unsubstituted phenyl group being more preferable. In this case, the remaining $R^{11}$, $R^{12}$, $R^{14}$ to $R^{16}$ and $R^{18}$ are hydrogen.

The compound represented by the formula (10) in which $Ar^5$ and $Ar^6$ (phenyl, in particular) are bonded to the m-position has a small broadening of the conjugated system relative to the amine part as compared with the compound in which $Ar^5$ and $Ar^6$ are bonded to the p-position. In addition, the electron donating property to the amine part is suppressed, and hence, this compound tends to have a shorter wavelength. As a result, color purity is improved. Further, in the molecular structure, flatness is improved three-dimensionally, whereby energy transfer with a host atom is conducted efficiently, resulting in tendency of improvement in efficiency.

Specific preferable compounds of the phenyl-substituted anthracene derivative represented by the formula (2) used in the organic emission medium of the invention are shown below.

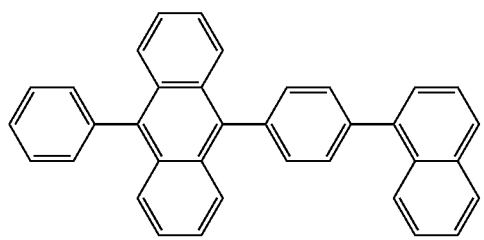

EM-1

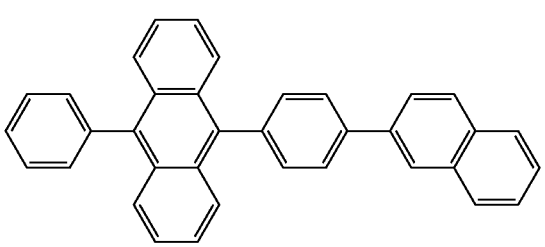

EM-2

-continued
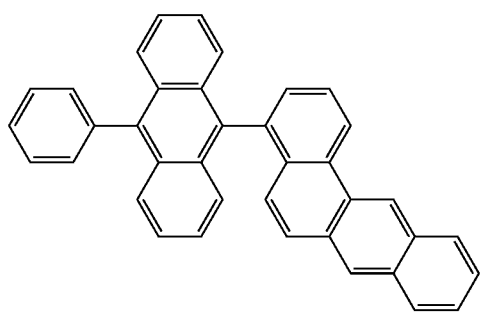
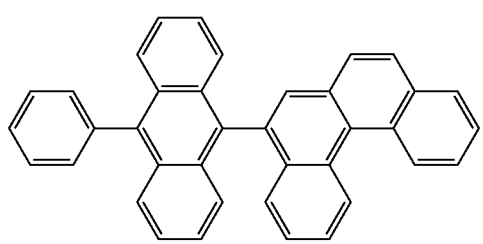
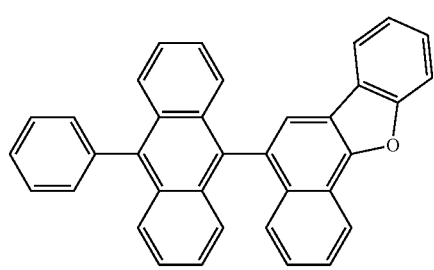
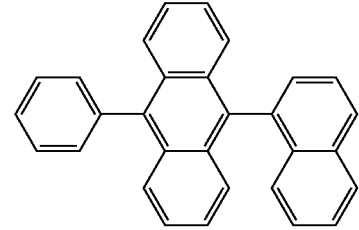
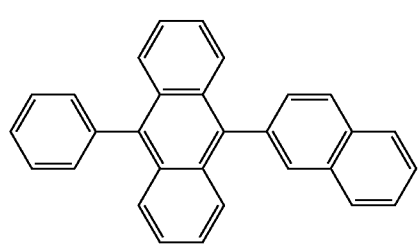
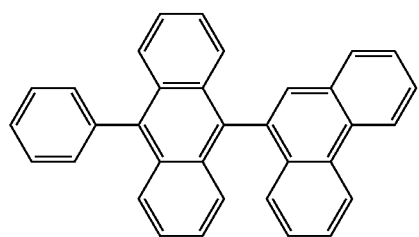
-continued
EM-3
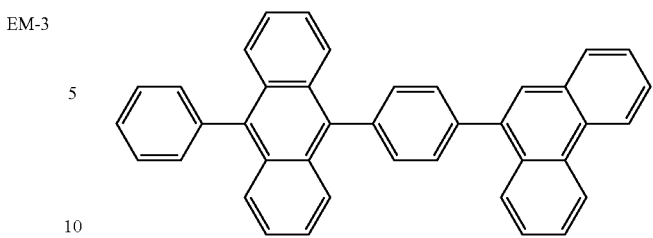
EM-4
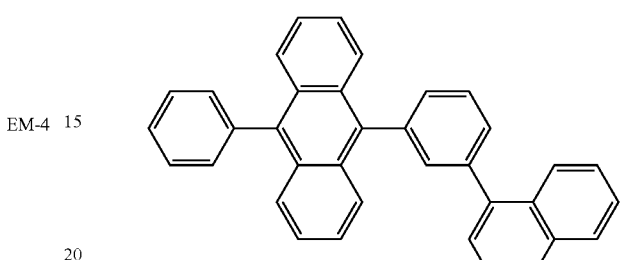
EM-5
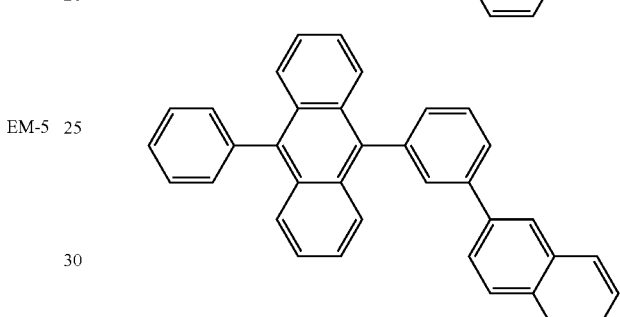
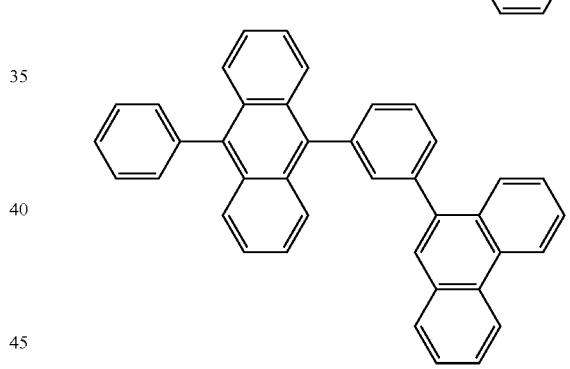
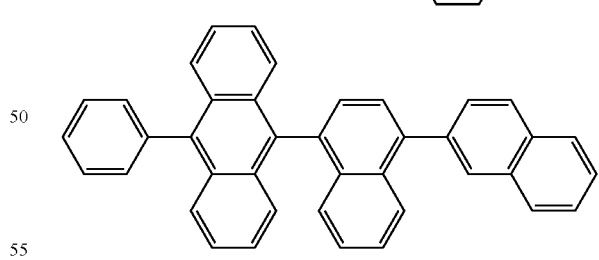
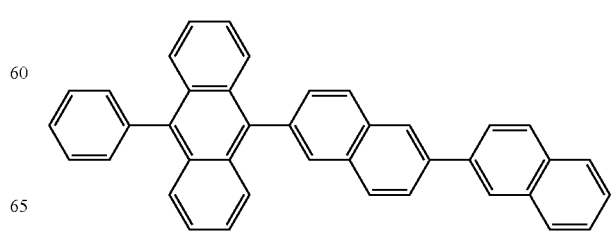

-continued
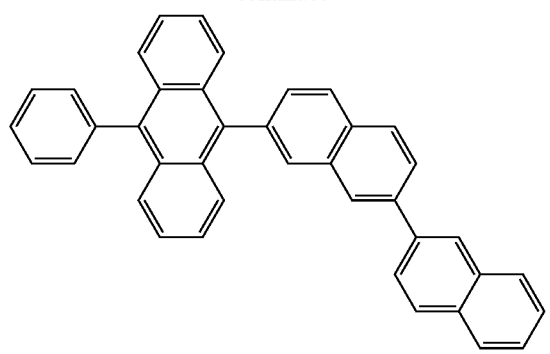
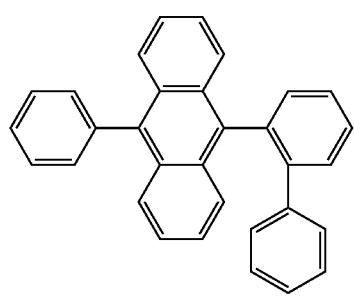
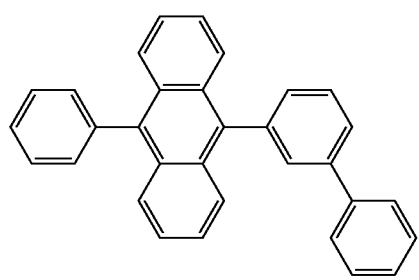
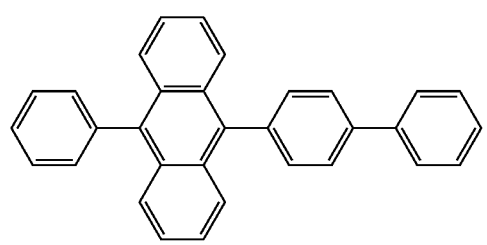
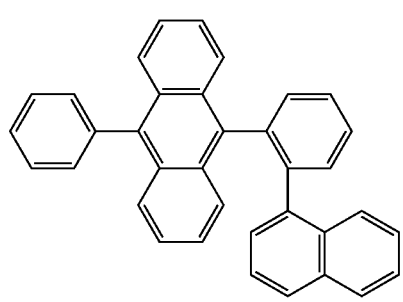
-continued
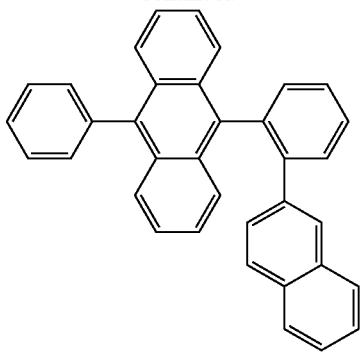
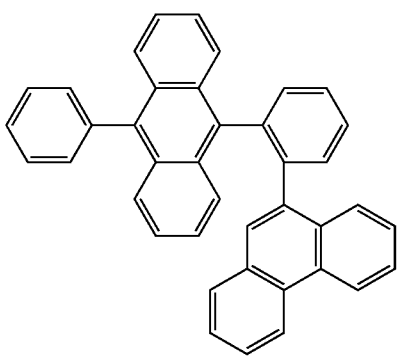
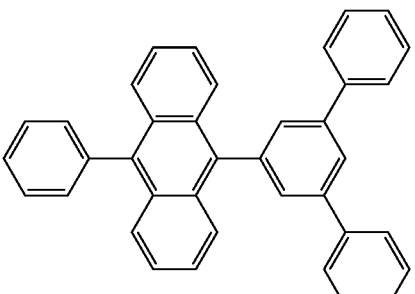
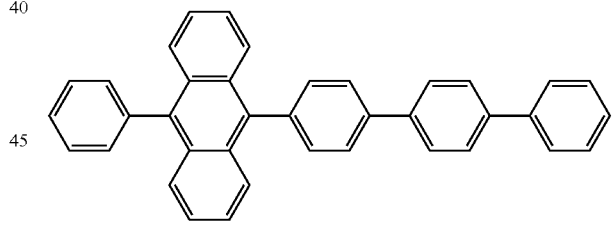
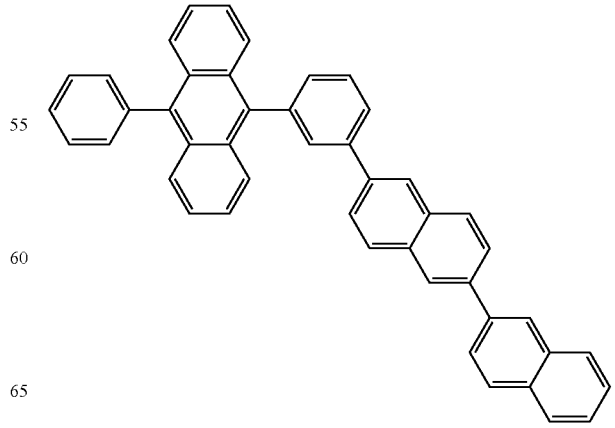

-continued
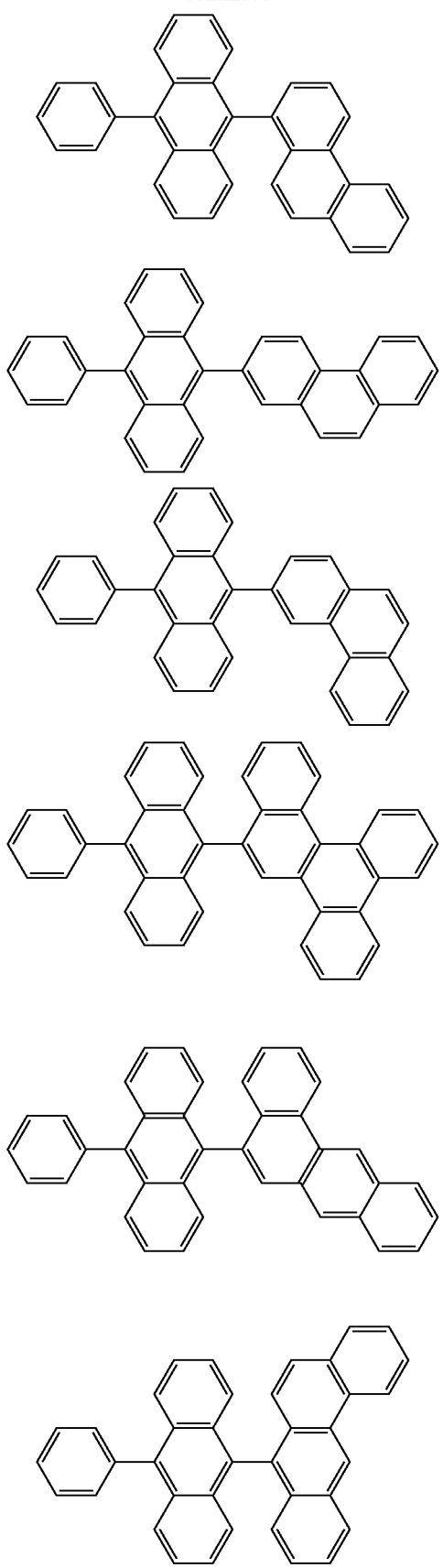
-continued
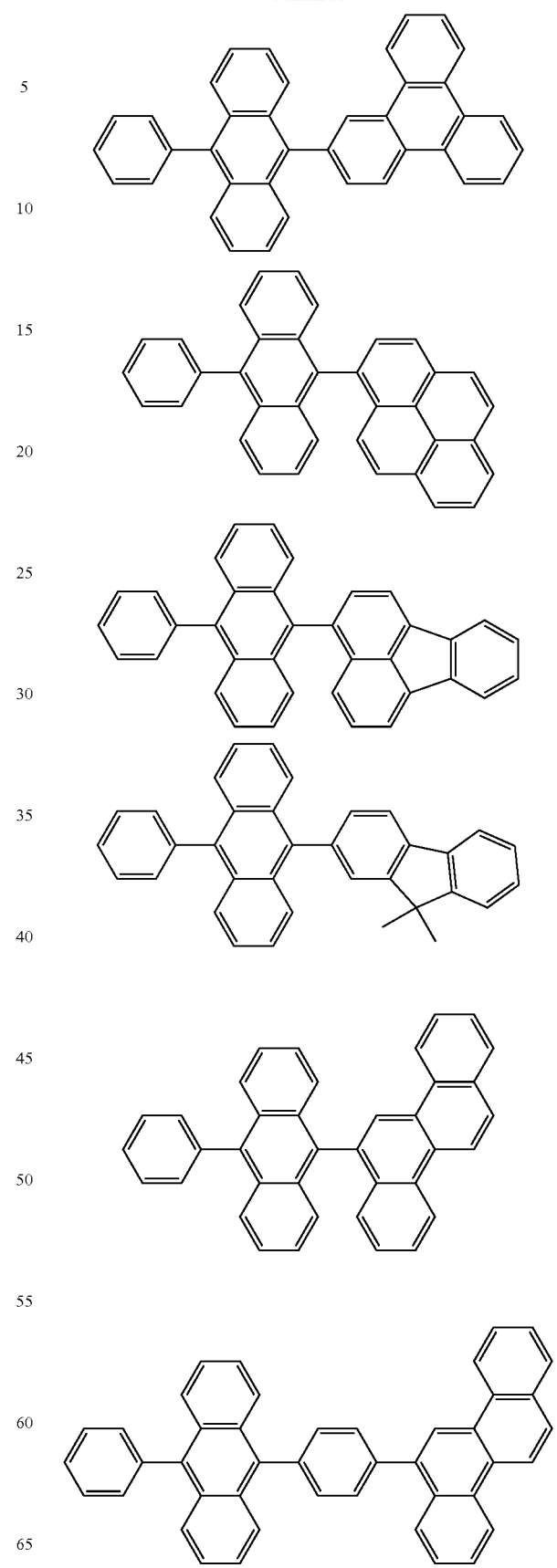

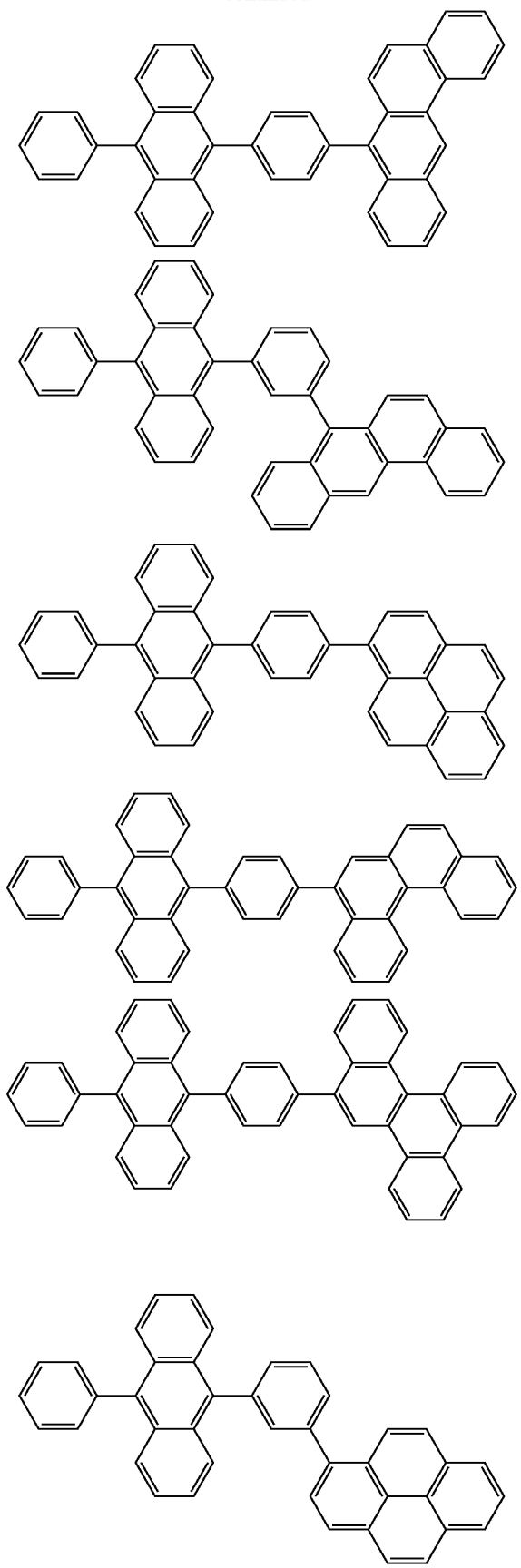
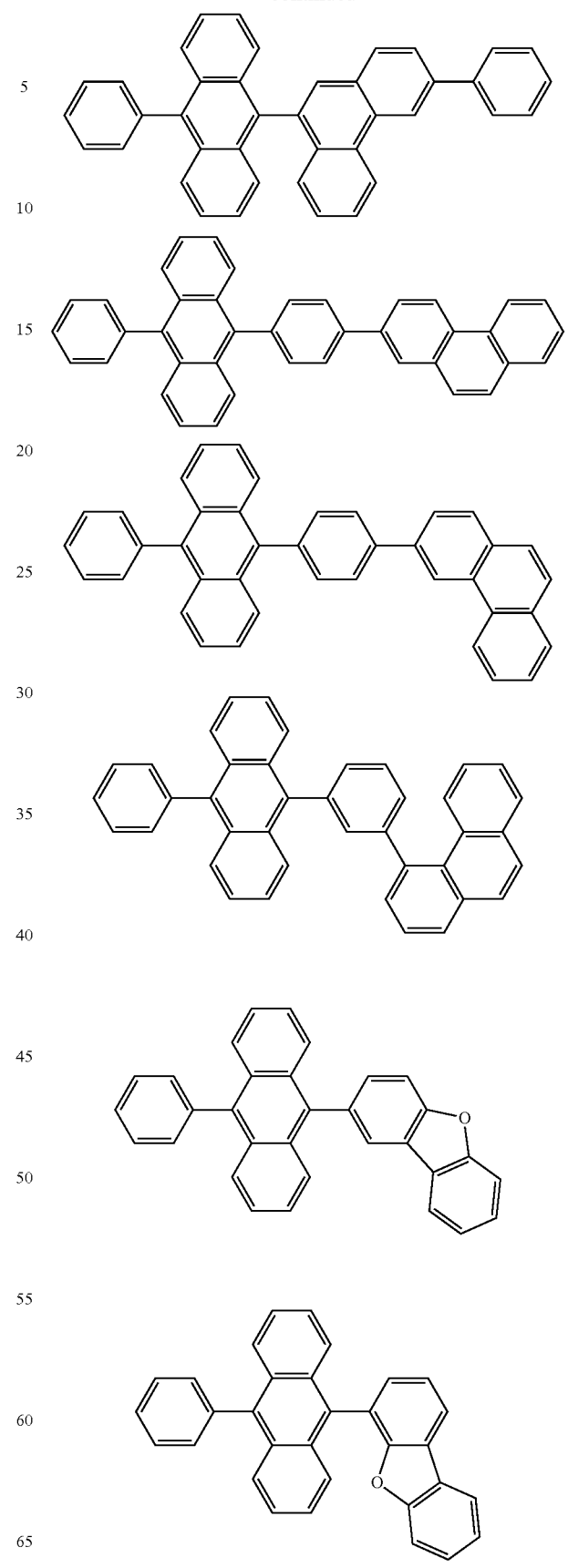

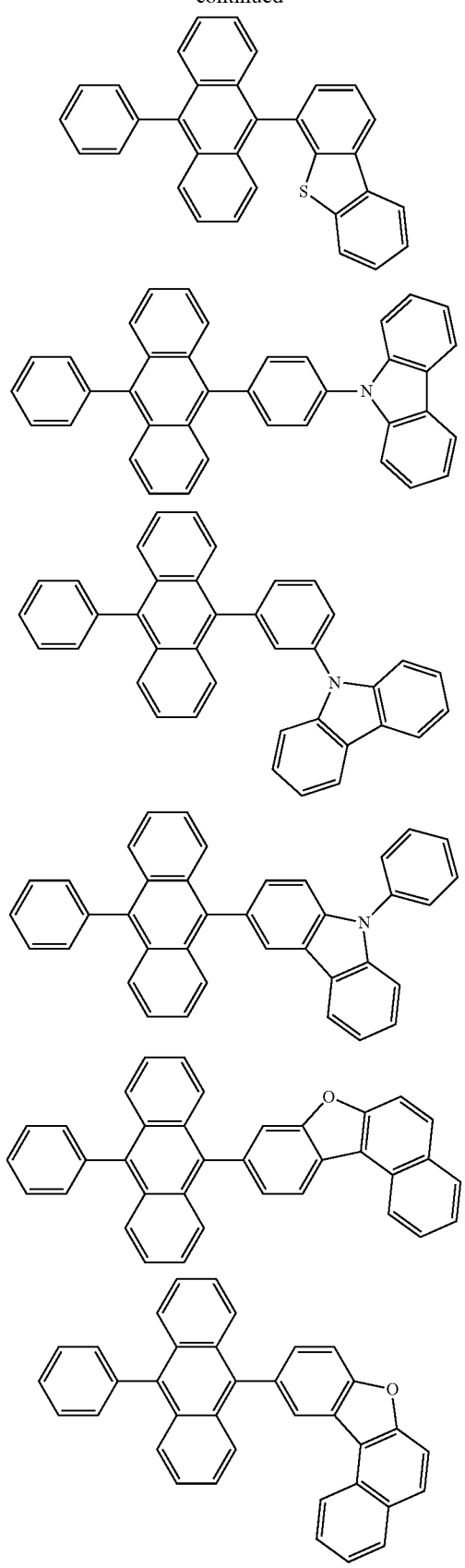
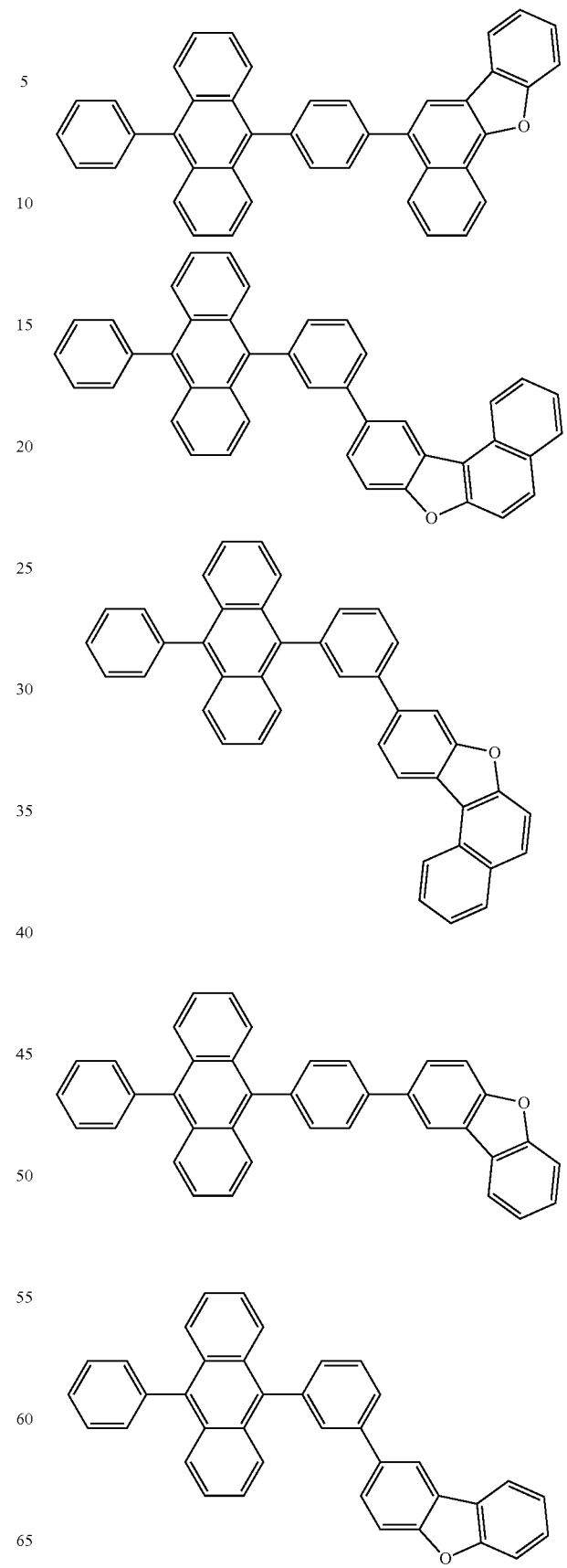

37
-continued
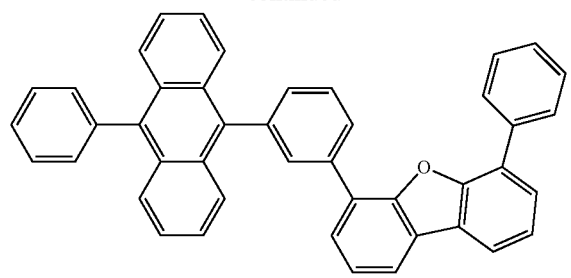
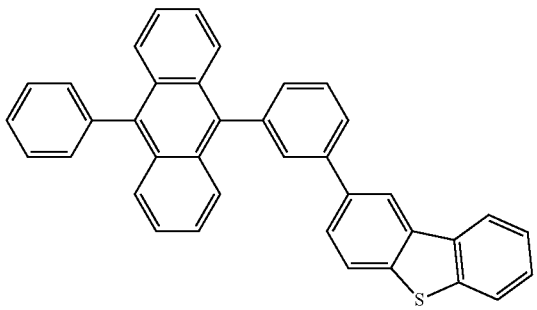
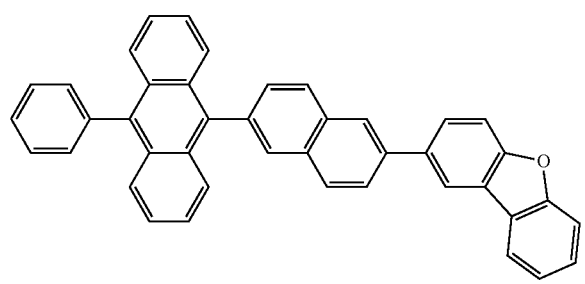
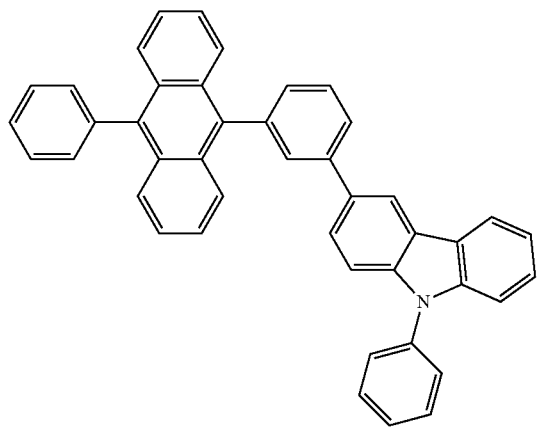
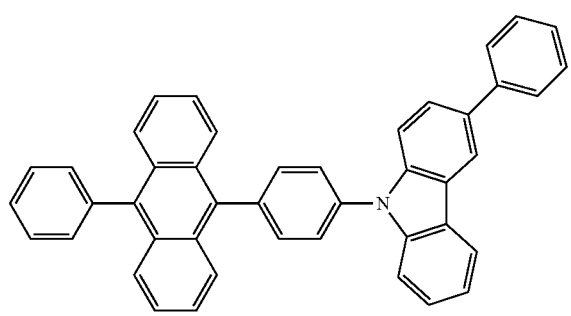
38
-continued
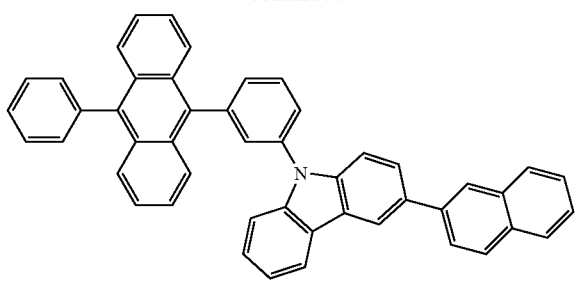
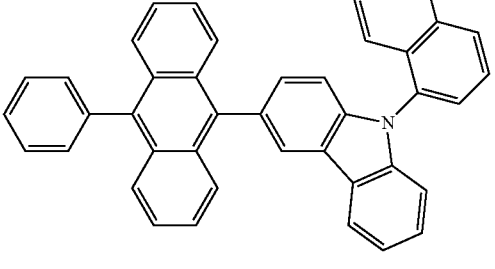
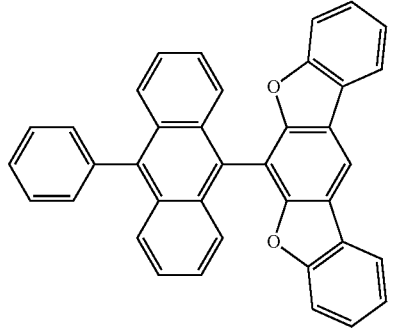
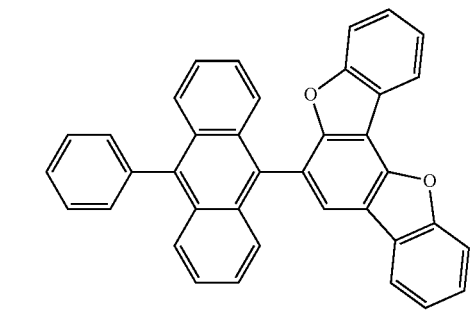
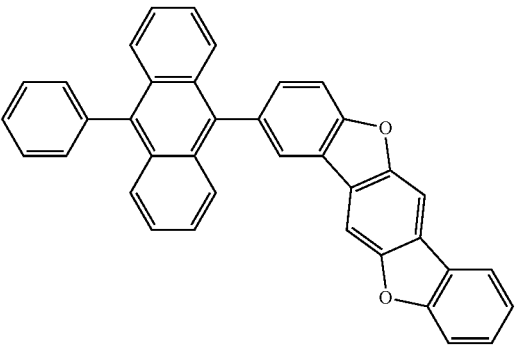

-continued
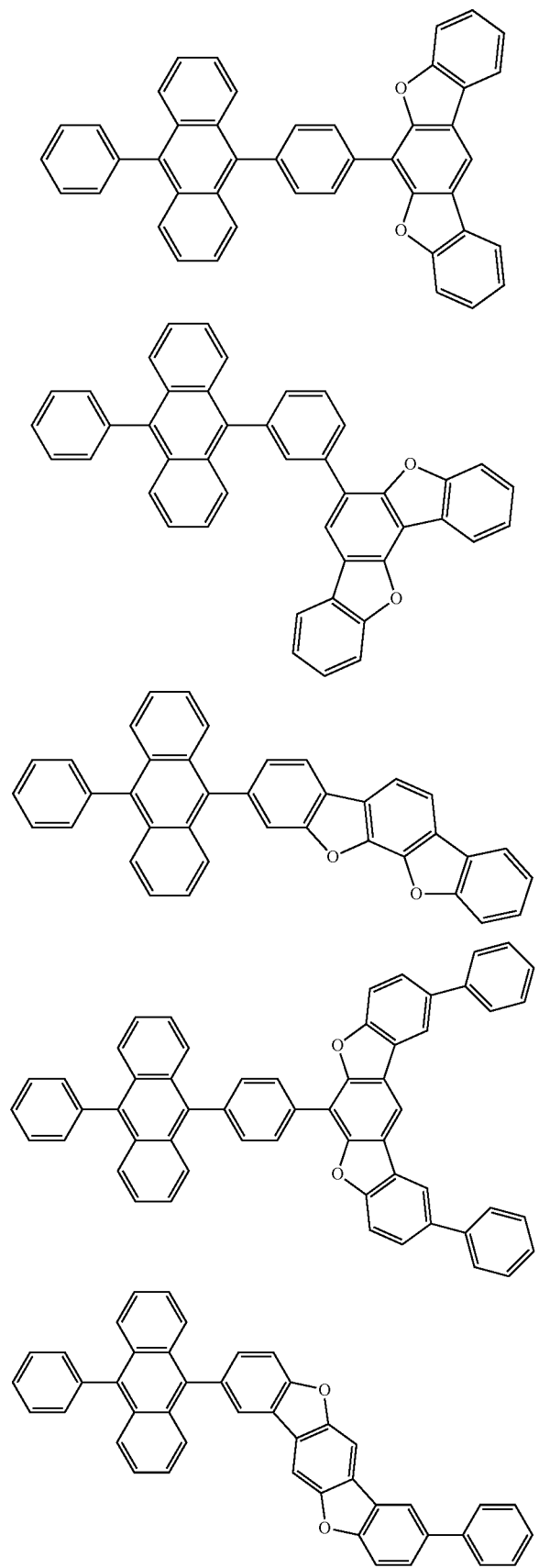
-continued
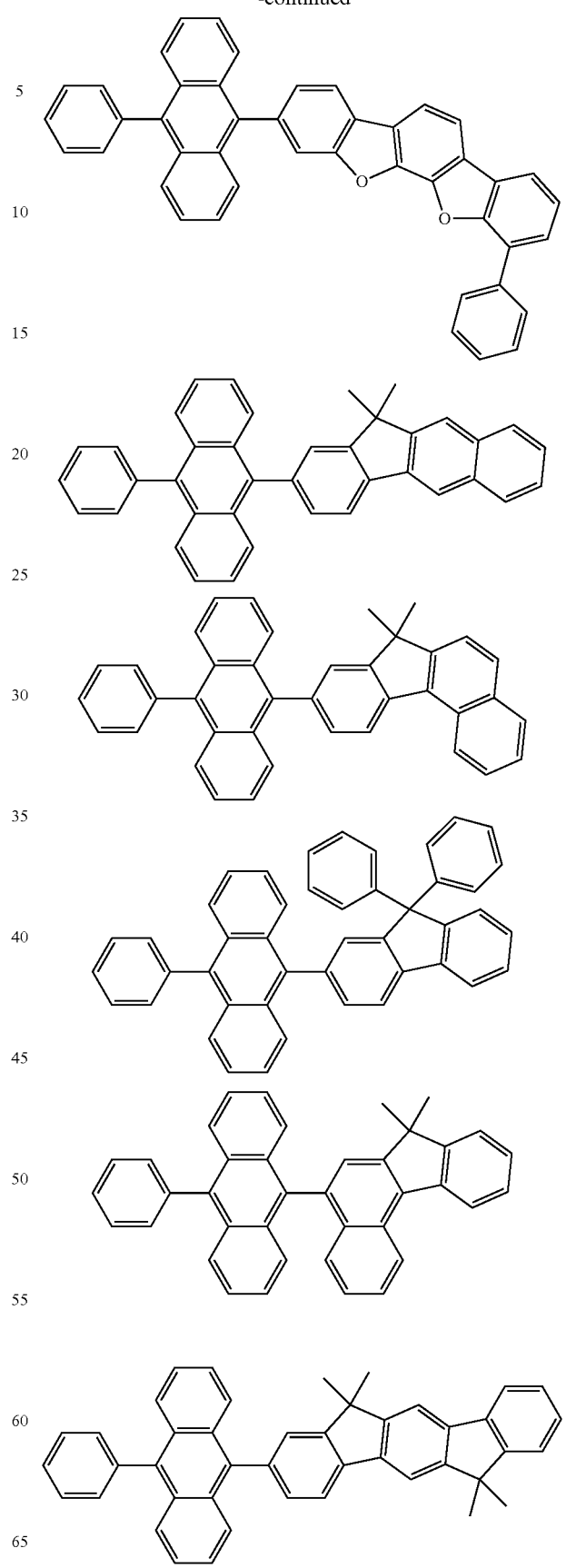

-continued

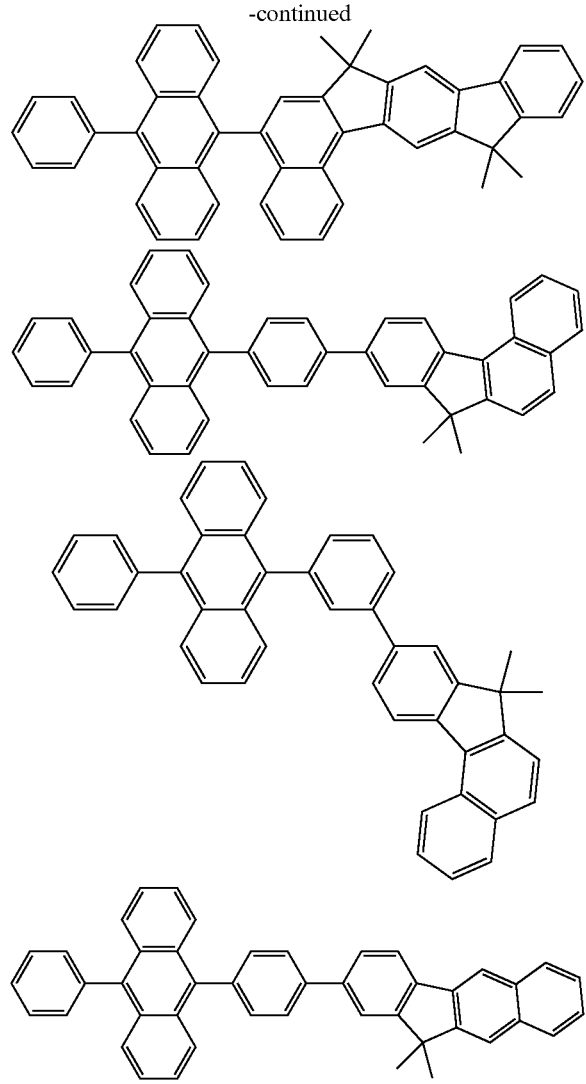

An organic light-emitting medium in which at least one of the pyrene derivatives represented by the above formula (1) is used as a doping material (dopant) and at least one of the phenyl-substituted anthracene derivatives represented by the above formula (2) is used as a host material has a high luminous efficiency and has a long lifetime. By using this light-emitting medium as an emitting layer of an organic electroluminescence device or the like, a device having a high luminous efficiency and a long life can be obtained.

In the organic light-emitting medium of the invention, in order to allow it to be a light-emitting medium having a high luminous efficiency and a long lifetime without impairing the advantageous effects, in addition to the above-mentioned pyrene derivative and the phenyl-substituted anthracene derivative, various materials may be contained. As for the materials which can be contained, an explanation will be made later in the explanation of the organic electroluminescence device of the invention, given later.

II. Organic Electroluminescence Device

In the organic electroluminescence device of the invention (hereinafter referred to as the organic EL device of the invention), one or more organic thin films including an emitting layer are disposed between an anode and a cathode.

The emitting layer includes the organic light-emitting medium of the invention or the pyrene derivative represented by the formula (10). If the emitting layer includes the pyrene derivative represented by the formula (10), it is preferred that the derivative of the formula (2) be contained as a host together.

In the organic EL device of the invention, the emitting layer comprises a host material and a doping material if it is an organic layer having an emitting function and has a doping system. At this time, the host material mainly promotes re-combination of electrons and holes and has a function of confining excitons in the emitting layer. The dopant material has a function of allowing the excitons obtained by re-combination to emit light efficiently.

Easiness in injecting of holes and electrons to the emitting layer may differ. Further, the hole-transporting capability and the electron-transporting capability which are shown by the mobility of holes and electrons in the emitting layer may differ.

As the method for forming an organic thin film layer, a known method such as a vapor deposition method, a spin coating method and an LB method can be used. An organic thin film layer can be formed by a method in which a binder such as a resin and a material compound are dissolved in a solvent to obtain a solution, and this solution is formed into a thin film by a spin coating method or the like.

If a plurality of organic thin film layers is formed, they may be formed by the same method or by two or two or more methods.

In the invention, as an organic EL device having a plurality of organic thin film layers, the following stacked structures can be given.

(anode/hole-injecting layer/emitting layer/cathode), (anode/emitting layer/electron-injecting layer/cathode), (anode/hole-injecting layer/emitting layer/electron-injecting layer/cathode), (anode/hole-injecting layer/hole-transporting layer/emitting layer/electron-injecting layer/cathode), (anode/hole-injecting layer/hole-transporting layer/emitting layer/electron-transporting layer/electron-injecting layer/cathode), etc.

The organic EL device of the invention may have a tandem device structure in which at least two emitting layers are provided. Specific examples of the device structure are shown below.

Anode/first emitting layer/intermediate layer/second emitting layer/electron-transporting region/cathode Anode/first emitting layer/electron-transporting region/intermediate layer/second emitting layer/cathode Anode/first emitting layer/electron-transporting region/intermediate layer/second emitting layer/electron-transporting region/cathode Anode/first emitting layer/intermediate layer/second emitting layer/electron-transporting region/cathode Anode/first emitting layer/electron-transporting region/intermediate layer/second emitting layer/cathode Anode/first emitting layer/carrier-blocking layer/second emitting layer/electron-transporting region/cathode Anode/first emitting layer/carrier-blocking layer/second emitting layer/third emitting layer/electron-transporting region/cathode The organic light-emitting medium of the invention or the pyrene derivative of the formula (10) can be used in one or two or more of these emitting layers. Further, for other emitting layers, an organic light-emitting medium using other fluorescent materials or an organic light-emitting medium using phosphorescent materials can be used.

By allowing an organic thin film layer to be formed of a plurality of layers, an organic EL device can be prevented from lowering in luminance or lifetime by quenching. A hole-injecting layer, an emitting layer and an electron-injecting layer may respectively be formed of two or more layers. In this case, in the case of a hole-injecting layer, a layer for injecting holes from an electrode is called a hole-injecting layer, and a layer which receives holes from the hole-injecting layer and transports to the emitting layer is called a hole-transporting layer. Similarly, in the case of an electron-injecting layer, a layer for injecting electrons from an electrode is called an electron-injecting layer and a layer for receiving electrons from an electron-injecting layer and transporting electrons to an emitting layer is called an electron-transporting layer. Each of these layers is selected for use in view of the factors such as the energy level of the material, the heat resistance, adhesion with an organic layer or a metal electrode or the like.

As the material which can be used in the emitting layer which does not use the organic emitting medium of the invention or the pyrene derivative of the formula (10), fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene and derivatives thereof, organic metal complexes such as tris(8-quinolinolato)aluminum, triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acrylidone derivatives and quinacrylidone derivatives can be used, for example.

The above-mentioned compounds can be used in the emitting layer which uses the organic light-emitting medium of the invention or the pyrene derivative represented by the formula (10) as long as it does not impair attaining the object of the invention.

As the hole-injecting material, a compound which can transport holes, exhibits hole-injecting effect from the anode and excellent hole-injection effect for the emitting layer or the emitting material, and has an excellent capability of forming a thin film is preferable. Specific examples thereof include, though not limited thereto, phthalocyanine derivatives, naphthalocyanine derivatives, porphyline derivatives, benzidine-type triphenylamine, diamine-type triphenylamine, hexacyanohexaazatriphenylene, derivatives thereof, and polymer materials such as polyvinylcarbazole, polysilane and conductive polymers.

Of the hole-injecting materials usable in the organic EL device of the invention, further effective hole-injecting materials are phthalocyanine derivatives.

Examples of the phthalocyanine (Pc) derivative include, though not limited thereto, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc, and naphthalocyanine derivatives.

In addition, it is also possible to sensitize carriers by adding to the hole-injecting material an electron-accepting substance such as a TCNQ derivative.

Preferable hole-transporting materials usable in the organic EL device of the invention are aromatic tertiary amine derivatives.

Examples of the aromatic tertiary amine derivative include, though not limited thereto, N,N'-diphenyl-N,N'-dinaphthyl-1,1'-biphenyl-4,4'-diamine, N,N,N',N'-tetrabiphenyl-1,1'-biphenyl-4,4'-diamine or an oligomer or a polymer having these aromatic tertiary amine skeletons.

As the electron-injecting material, a compound which can transport electrons, exhibits electron-injecting effect from the cathode and excellent electron-injection effect for the emitting layer or the emitting material, and has an excellent capability of forming a thin film is preferable.

In the organic EL device of the invention, further effective electron-injecting materials are a metal complex compound and a nitrogen-containing heterocyclic derivative.

Examples of the metal complex compound include, though not limited thereto, 8-hydroxyquinolinate lithium, bis(8-hydroxyquinolinate)zinc, tris(8-hydroxyquinolinate)aluminum, tris(8-hydroxyquinolinate)gallium, bis(10-hydroxybenzo[h]quinolinate)beryllium and bis(10-hydroxybenzo[h]quinolinate)zinc.

As examples of the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable, for example. Of these, a benzimidazole derivative, a phenanthroline derivative and an imidazopyridine derivative are preferable.

As a preferred embodiment, a dopant is further contained in these electron-injecting materials, and in order to facilitate receiving electrons from the cathode, it is further preferable to dope the vicinity of the cathode interface of the second organic layer with a dopant, the representative example of which is an alkali metal.

As the dopant, a donating metal, a donating metal compound and a donating metal complex can be given. These reducing dopants may be used singly or in combination of two or more.

In addition, for improving stability of the organic EL device obtained by the invention to temperature, humidity, atmosphere, etc. it is also possible to prepare a protective layer on the surface of the device, and it is also possible to protect the entire device by applying silicone oil, resin, etc.

As the conductive material used in the anode of the organic EL device of the invention, a conductive material having a work function of more than 4 eV is suitable. Carbon, aluminum, vanadium, iron, cobalt, nickel, tungsten, silver, gold, platinum, palladium or the like, alloys thereof, oxidized metals which may be used in an ITO substrate and a NESA substrate such as tin oxide and indium oxide and organic conductive resins such as polythiophene and polypyrrole are used.

As the conductive material used in the cathode, a conductive material having a work function of smaller than 4 eV is suitable. Magnesium, calcium, tin, lead, titanium, yttrium, lithium, ruthenium, manganese, aluminum, and lithium fluoride or the like, and alloys thereof are used, but not limited thereto. Representative examples of the alloys include, though not limited thereto, magnesium/silver alloys, magnesium/indium alloys and lithium/aluminum alloys. The amount ratio of the alloy is controlled by the temperature of the deposition source, atmosphere, vacuum degree or the like, and an appropriate ratio is selected. If necessary, the anode and the cathode each may be composed of two or more layers.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is formed such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given.

Each layer of the organic EL device of the invention can be formed by a dry film-forming method such as vacuum vapor deposition, sputtering, plasma coating, ion plating or the like or a wet film-forming method such as spin coating, dipping, flow coating or the like. Although the film thickness is not particularly limited, it is required to adjust the film thickness to an appropriate value. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied. The suitable film thickness is normally 5 nm to 10 μm, with a range of 10 nm to 0.2 μm being further preferable.

In the case of the wet film-forming method, a thin film is formed by dissolving or dispersing materials forming each layer in an appropriate solvent such as ethanol, chloroform, tetrahydrofuran and dioxane. Any of the above-mentioned solvents can be used.

As the solvent suited to such a wet film-forming method, a solution containing the pyrene derivative of formula (1) and phenyl-substituted anthracene of the formula (2) as an organic EL material and a solvent can be used.

In each organic thin film layer, an appropriate resin or additive may be used in order to improve film-forming properties, to prevent generation of pinholes in the film, or for other purposes.

EXAMPLES

Hereinbelow, the invention will be described in more detail with reference to the following examples which should not be construed as limiting the scope of the invention.

Synthesis Example 1: Synthesis of Compound D-1

Compound D-1 was synthesized according to the following scheme.

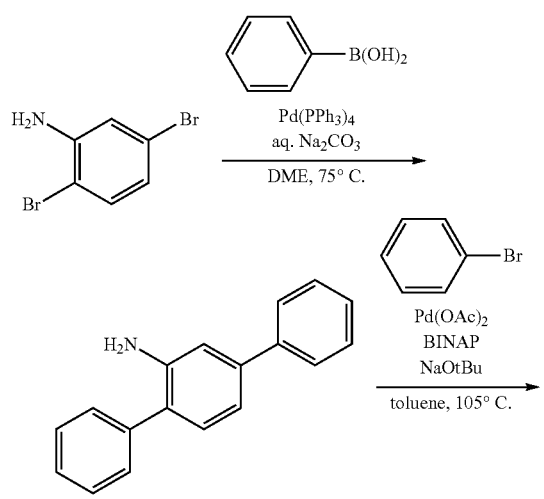

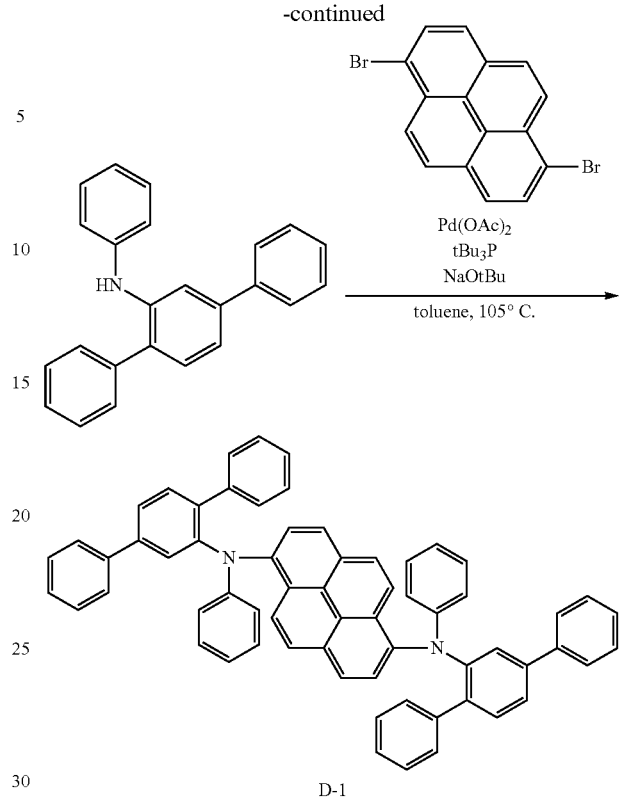

D-1

(a) Synthesis of 2,5-diphenylaniline

Under an argon atmosphere, a mixture of 2,5-dibromoaniline (150 g, 0.598 mol), phenylboronic acid (160 g, 1.79 mol), tetrakis(triphenylphosphine)palladium (0) (27.6 g, 0.0234 mol), a 2M aqueous sodium carbonate solution (900 mL, 1.80 mol) and 1,2-dimethoxyethane (3.5 L) was stirred at 75° C. for 23 hours. The reaction mixture was cooled to the room temperature. Then, water was added, and precipitated solids were collected by filtration. The resulting solids were purified by silica gel column chromatography, whereby 119 g (81%) of an intended 2,5-diphenylaniline was obtained.

(b) Synthesis of N-phenyl-2,5-diphenylaniline

A mixture of bromobenzene (36.4 g, 232 mmol), 2,5-diphenylaniline (114 g, 464 mmol), synthesized in (a) palladium acetate (II) (1.56 g, 6.96 mmol), 8.67 g (13.9 mmol) of BINAP (2,2'-bis(diphenylphosphino)-1,1'-binaphthyl racemic body and 1.5 L of toluene were heated to 90° C. under an argon atmosphere. Then, sodium tert-butoxide (44.6 g, 464 mmol) was added, and the resulting mixture was stirred at 105° C. for 5 hours under an argon atmosphere. The reaction mixture was cooled to room temperature, and water was added to allow the mixture to separate into two liquids. The solvent of the resulting organic layer was concentrated by reducing pressure, and the thus obtained solids were purified by silica gel chromatography, whereby 66.6 g (yield: 85%) of an intended N-phenyl-2,5-diphenylaniline was obtained.

(c) Synthesis of Compound D-1

A mixture of 1,6-dibromopyrene (23.2 g, 64.5 mmol), N-phenyl-2,5-diphenylaniline (45.6 g, 142 mmol) synthesized in (b), palladium acetate (0.6 g, 2.67 mmol), tri-tert-butylphosphine (1.08 g, 5.33 mmol) and toluene (700 ml) was heated to 90° C. under an argon atmosphere. Then, sodium tert-butoxide (15.4 g, 160 mmol) was added, and stirred at 105° C. for 3 hours under an argon atmosphere. The reaction mixture was cooled to room temperature, the purified solids were collected by filtration. The thus obtained solids were purified by silica gel chromatography, then purified by re-crystallization, whereby 33.7 g (yield: 62%) of an intended compound D-1 was obtained.

As a result of mass spectrometry, the resulting compound was identified as the compound D-1 (m/e=840 relative to the molecular weight of 840.35).

Example 1

On a glass substrate of 25 mm by 75 mm by 1.1 mm thick, a transparent electrode of an indium tin oxide was formed into a thickness of 120 nm. This transparent electrode serves as an anode. Subsequently, this glass substrate was cleaned by irradiating with UV rays and ozone, and the cleaned glass substrate was mounted in a vacuum deposition apparatus.

On the anode, as a hole-injecting layer, compound HT-1 was deposited in a thickness of 50 nm. On this layer, as a hole-transporting layer, compound HT-2 was deposited in a thickness of 45 nm. Then, an anthracene derivative EM-1 as the host material and the compound D-1 as the doping material were co-deposited in a mass ratio of 25:5, whereby an emitting layer with a thickness of 30 nm was formed. On this emitting layer, as an electron-injecting layer, compound ET-1 was deposited in a thickness of 25 nm. Subsequently, lithium fluoride was deposited in a thickness of 1 nm, and then, aluminum was deposited in a thickness of 150 nm, whereby an organic EL device was fabricated. This aluminum/lithium fluoride film serves as a cathode.

Compound HT-1, compound HT-2 and compound ET-1 used in the production of the organic EL device are compounds having the following structure.

HT-1

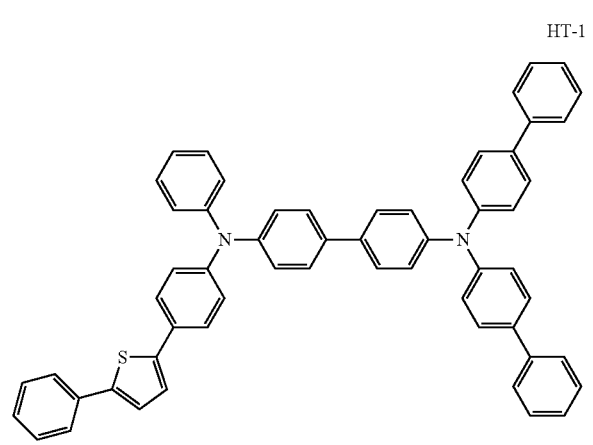

HT-2

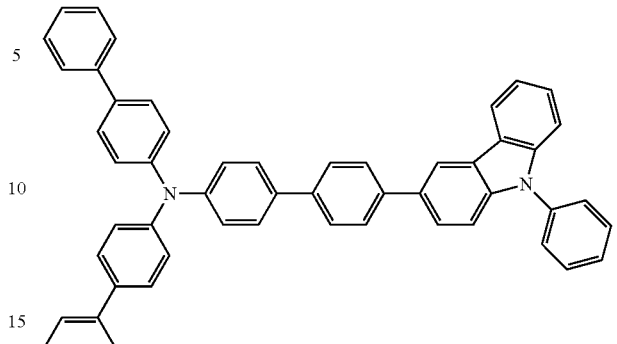

ET-1

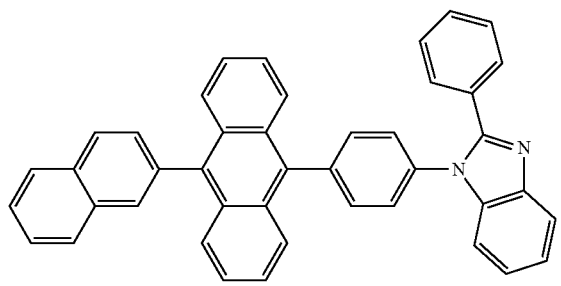

For the resulting organic EL, the device performance (external quantum yield (%)) at the time of deriving at a current density of 10 mA/cm² and the lifetime (hr) for which the luminance was decreased by 80% from the initial luminance at a current density of 50 mA/cm² were evaluated. The results are shown in Table 1.

The external quantum efficiency (E.Q.E) was measured by the following method.

Current having a current density of 10 mA/cm² was applied to the resulting organic EL device. Emission spectra thereof were measured with a spectroradiometer (CS1000, produced by MINOLTA), and the external quantum yield was calculated by the following formula.

$$E.Q.E = \frac{N_P}{N_E} \times 100$$

$$= \frac{\frac{(\pi/10^9)\int \phi(\lambda)\cdot d\lambda}{hc}}{\frac{J/10}{e}} \times 100$$

$$= \frac{\frac{(\pi/10^9)\sum (\phi(\lambda)\cdot(\lambda))}{hc}}{\frac{J/10}{e}} \times 100 \ (\%)$$

$N_P$: Number of photons
$N_E$: Number of electrons
$\pi$: Circular constant=3.1416
$\lambda$: Wavelength (nm)
$\varphi$: Luminescence intensity (W/sr·m²·nm)
h: Planck constant=6.63×10⁻³⁴ (J·s)
c: Light velocity=3×10⁸ (m/s)
J: Current density (mA/cm²)
e: Charge=1.6×10⁻¹⁹ (C)

Examples 2 to 15 and Comparative Examples 1 to 11

Organic EL devices were fabricated in the same manner as in Example 1, except that the doping materials and the host materials were changed to the compounds shown in Table 1, and the external quantum yield (%) and the lifetime (hour) were evaluated. The results are shown in Table 1.

The structural formulas of the compounds used as the doping material and the host material in the emitting layers of the organic EL devices produced in the Examples and the Comparative Examples are shown below.

(Doping material)

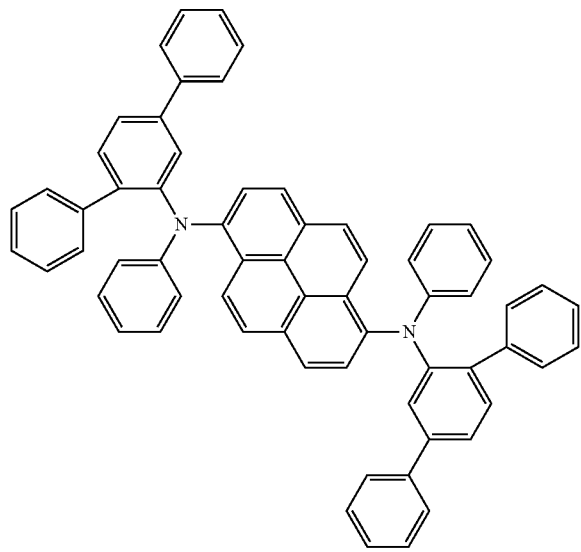

D-1

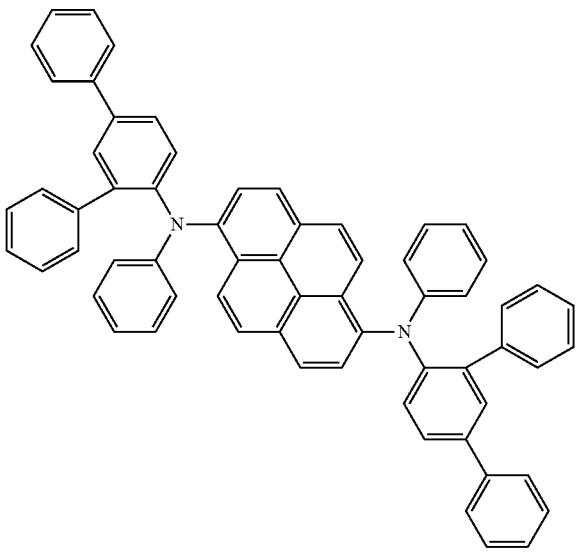

D-2

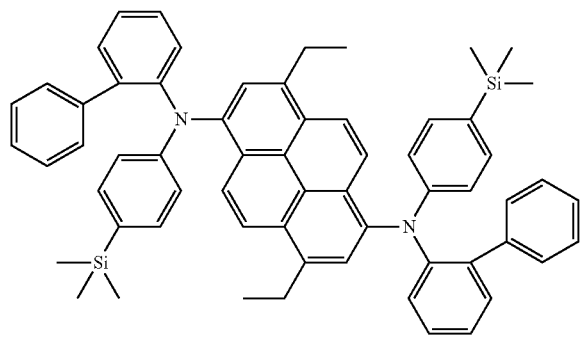

D-3

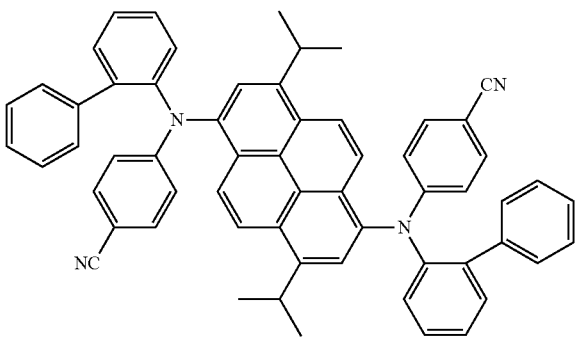

D-4

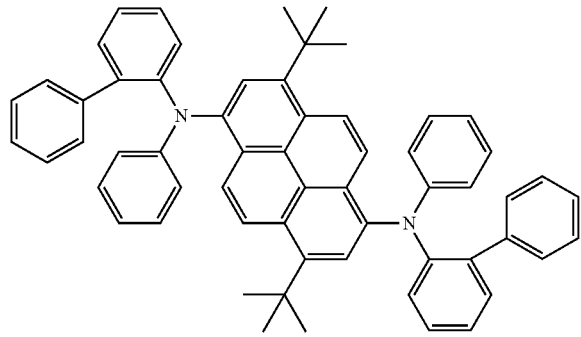

D-5

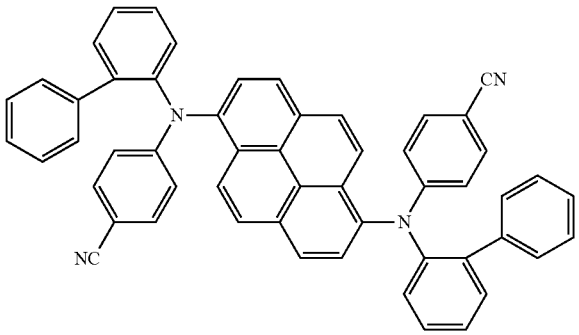

D-6

-continued
D-7
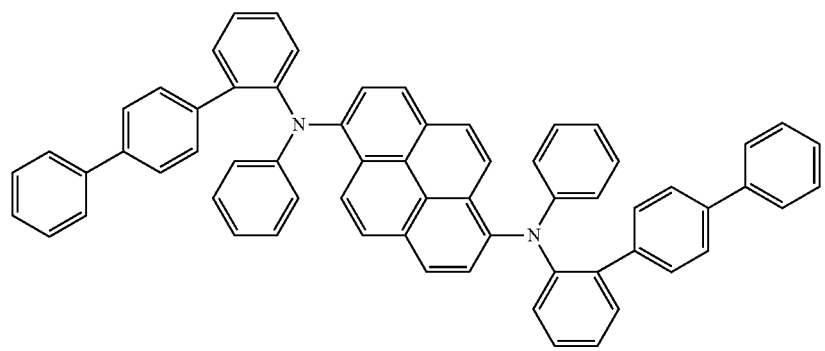
HD-1
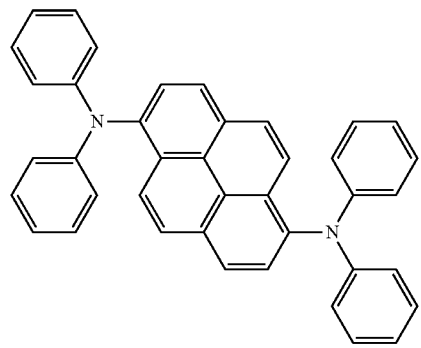
HD-2
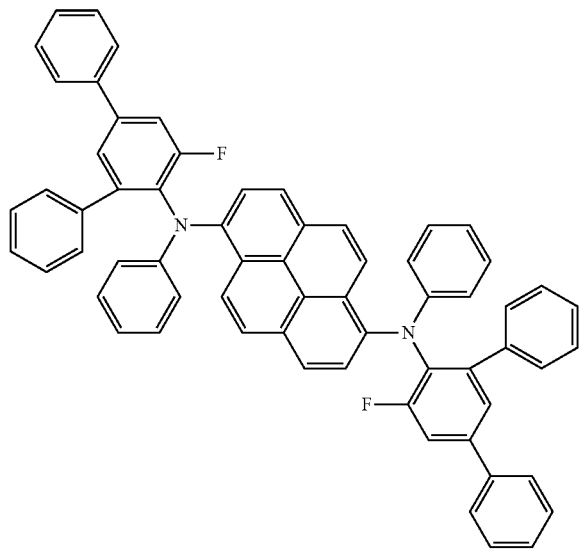
(Host material)
HD-3
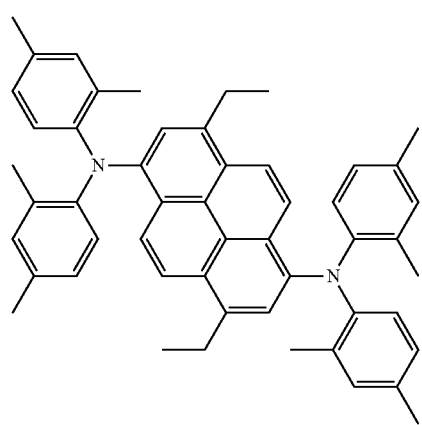
EM-1
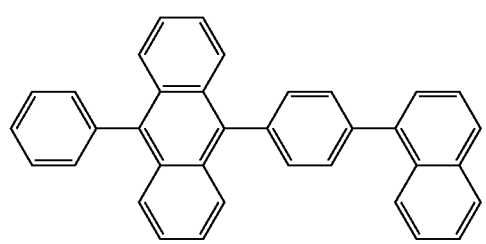

-continued
EM-2
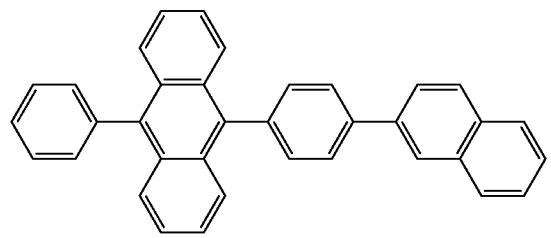
EM-3
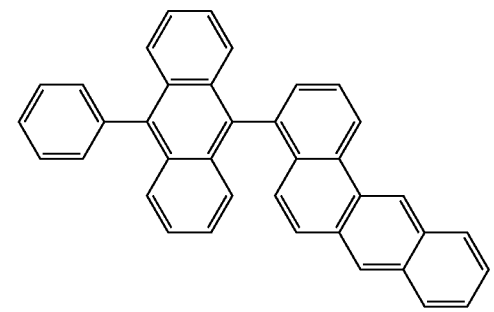
EM-4
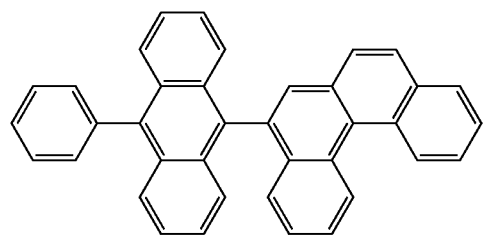
EM-5
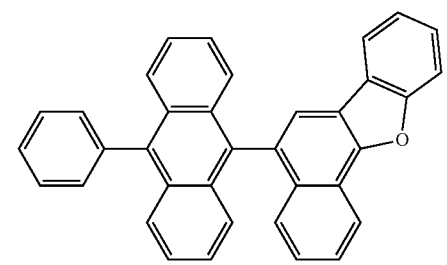
H-1
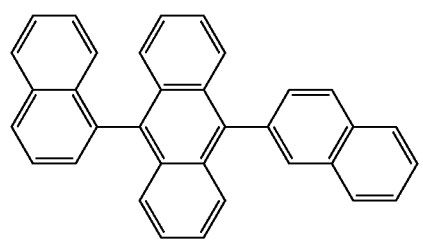
H-2
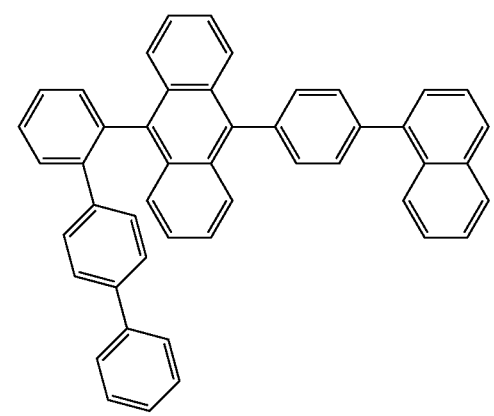
H-3
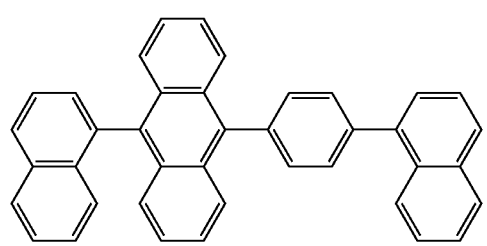
TABLE 1
| Examples | Doping material | Host material | External quantum yield (%) | Lifetime (hr) |
|---|---|---|---|---|
| Example 1 | D-1 | EM-1 | 8.6 | 130 |
| Example 2 | D-1 | EM-2 | 8.5 | 110 |
| Example 3 | D-1 | EM-3 | 8.5 | 160 |
| Example 4 | D-1 | EM-4 | 9.1 | 140 |
| Example 5 | D-2 | EM-2 | 8.2 | 130 |
| Example 6 | D-3 | EM-1 | 7.5 | 100 |
| Example 7 | D-3 | EM-2 | 7.8 | 130 |
| Example 8 | D-3 | EM-3 | 8.2 | 100 |
| Example 9 | D-4 | EM-1 | 8.3 | 130 |
| Example 10 | D-4 | EM-2 | 8.0 | 120 |
| Example 11 | D-5 | EM-2 | 7.9 | 110 |
| Example 12 | D-5 | EM-3 | 7.7 | 110 |
| Example 13 | D-5 | EM-5 | 8.2 | 110 |
| Example 14 | D-6 | EM-2 | 8.3 | 100 |
| Example 15 | D-7 | EM-1 | 8.6 | 100 |
| Com. Ex. 1 | D-2 | H-1 | 8.2 | 80 |
| Com. Ex. 2 | D-3 | H-1 | 8.2 | 80 |
| Com. Ex. 3 | D-4 | H-3 | 8.2 | 60 |
| Com. Ex. 4 | D-5 | H-2 | 7.7 | 65 |
| Com. Ex. 5 | D-6 | H-1 | 8.2 | 45 |

TABLE 1-continued

| Examples | Doping material | Host material | External quantum yield (%) | Lifetime (hr) |
|---|---|---|---|---|
| Com. Ex. 6 | HD-1 | EM-2 | 7.1 | 50 |
| Com. Ex. 7 | HD-1 | H-1 | 7.5 | 40 |
| Com. Ex. 8 | HD-1 | H-2 | 7.1 | 50 |
| Com. Ex. 9 | HD-2 | H-2 | 7.7 | 30 |
| Com. Ex. 10 | HD-3 | EM-1 | 7.7 | 80 |
| Com. Ex. 11 | HD-2 | EM-1 | 8.4 | 30 |

From the results shown in Table 1, when the pyrene derivative represented by the formula (1) was used as a doping material and the phenyl-substituted anthracene derivative represented by the formula (2 was used as a host material, a high external quantum yield (%) and a long lifetime can be attained.

We consider that, in the invention, by using a pyrene derivative having a specific structure and a phenyl-substituted anthracene derivative having a specific structure in combination, carrier balance is improved and as a result, an organic EL device having a high luminous efficiency and a long life can be obtained.

INDUSTRIAL APPLICABILITY

The organic light-emitting medium of the invention is effective for producing a highly efficient and long-lived organic EL device.

The organic EL device of the invention can be suitably used as a planar emitting body such as a flat panel display of a wall-mounted television, for a copier, a printer, a backlight of a liquid crystal display, or instruments, a display panel, a sign board, and the like.

The organic light-emitting medium of the invention can be used not only in an organic EL device, but also in an electrophotographic photoreceptor, a photoelectric conversion device, a solar cell, an image sensor or the like.

Although only some exemplary embodiments and/or examples of this invention have been described in detail above, those skilled in the art will readily appreciated that many modifications are possible in the exemplary embodiments and/or examples without materially departing from the novel teachings and advantages of this invention. Accordingly, all such modifications are intended to be included within the scope of this invention.

The contents of the above-described documents are herein incorporated by reference in its entirety.

The invention claimed is:

1. A phenyl-substituted anthracene derivative represented by the following formula (2):

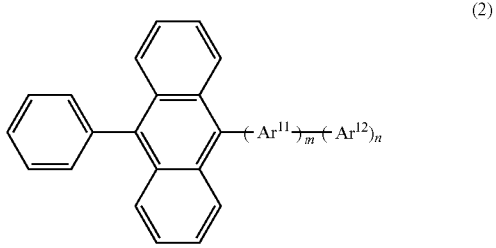

wherein
  $Ar^{11}$ is a substituted or unsubstituted naphthyl group,
  m is an integer of 1,
  $Ar^{12}$ is a substituted or unsubstituted 2-dibenzofuranyl group, and
  n is an integer of 1.

2. The phenyl-substituted anthracene derivative according to claim 1, wherein the substituent for the substituted or unsubstituted naphthyl group and the substituted or unsubstituted 2-dibenzofuranyl group is independently an alkyl group having 1 to 20 carbon atoms, or an aryl group having 6 to 30 ring carbon atoms.

3. The phenyl-substituted anthracene derivative according to claim 1, wherein the substituent for the substituted or unsubstituted naphthyl group and the substituted or unsubstituted 2-dibenzofuranyl group is a phenyl group.

4. The phenyl-substituted anthracene derivative according to claim 1, wherein $Ar^{11}$ is a substituted or unsubstituted 2,6-naphthalenediyl group.

5. The phenyl-substituted anthracene derivative according to claim 1, wherein $Ar^{11}$ is an unsubstituted 2,6-naphthalenediyl group.

6. The phenyl-substituted anthracene derivative according to claim 1, wherein $Ar^{11}$ is an unsubstituted 2-dibenzofuranyl group.

7. The phenyl-substituted anthracene derivative according to claim 1, wherein $Ar^{11}$ is an unsubstituted 2,6-naphthalenediyl group, and $Ar^{12}$ is an unsubstituted 2-dibenzofuranyl group.

8. An organic electroluminescence device comprising an anode and a cathode, and one or more organic thin film layers including an emitting layer between the anode and the cathode,
  the emitting layer comprising the phenyl-substituted anthracene derivative according to claim 1.

* * * * *